US008008322B2

(12) United States Patent
Ronan et al.

(10) Patent No.: US 8,008,322 B2
(45) Date of Patent: Aug. 30, 2011

(54) SUBSTITUTED PYRAZOLOPYRIDINES, COMPOSITIONS CONTAINING THEM, METHOD FOR THE PRODUCTION THEREOF, AND THEIR USE

(75) Inventors: Baptiste Ronan, Clamart (FR); Michel Tabart, La Norville (FR); Frank Halley, Chaville (FR); Eric Bacque, Gif sur Yvette (FR); Catherine Souaille, Choisy le Roi (FR); Antonio Ugolini, Massy (FR); Fabrice Viviani, Louvres (FR)

(73) Assignee: Aventis Pharma S.A., Antony (FR)

( * ) Notice: Subject to any disclaimer, the term of this patent is extended or adjusted under 35 U.S.C. 154(b) by 875 days.

(21) Appl. No.: 11/778,870

(22) Filed: Jul. 17, 2007

(65) Prior Publication Data

US 2008/0039491 A1 Feb. 14, 2008

Related U.S. Application Data

(63) Continuation of application No. PCT/FR2006/000114, filed on Jan. 18, 2006.

(30) Foreign Application Priority Data

Jan. 19, 2005 (FR) ..................................... 05 00555
Jul. 13, 2005 (FR) ..................................... 05 07505

(51) Int. Cl.
*A61K 31/437* (2006.01)
*A61P 35/00* (2006.01)
(52) U.S. Cl. ........................................ 514/303; 546/119
(58) Field of Classification Search .................. 546/119; 514/303
See application file for complete search history.

(56) References Cited

U.S. PATENT DOCUMENTS

| 6,562,811 | B1 | 5/2003 | Murata et al. | |
|---|---|---|---|---|
| 2004/0092546 | A1 | 5/2004 | Wei et al. | |
| 2004/0255397 | A1 | 12/2004 | Fessmann et al. | |
| 2007/0161626 | A1 | 7/2007 | Halley | |
| 2008/0058326 | A1* | 3/2008 | Hartung et al. | 514/234.2 |
| 2008/0064707 | A1* | 3/2008 | Hartung et al. | 514/253.04 |
| 2008/0182844 | A1 | 7/2008 | Bjergarde et al. | |

FOREIGN PATENT DOCUMENTS

| WO | WO 01/19828 A2 | 3/2001 |
|---|---|---|
| WO | WO 02/12242 A2 | 2/2002 |
| WO | WO 03/008405 A1 | 1/2003 |
| WO | WO 03/045949 A1 | 6/2003 |
| WO | WO 2004/009596 A2 | 1/2004 |
| WO | WO 2004/076450 A1 | 9/2004 |
| WO | WO 2004/096130 A2 | 11/2004 |
| WO | WO 2005/009389 A2 | 2/2005 |
| WO | 2005110410 * | 11/2005 |
| WO | WO 2005/110410 A2 | 11/2005 |
| WO | WO 2006/003276 | 1/2006 |
| WO | 2006050109 * | 5/2006 |
| WO | 2006077168 * | 7/2006 |
| WO | WO 2006/076442 A2 | 7/2006 |
| WO | WO 2006/099075 A2 | 9/2006 |
| WO | WO 2007/017577 A1 | 2/2007 |
| WO | WO 2007/056582 A1 | 5/2007 |
| WO | 2007144202 * | 12/2007 |
| WO | 2007144204 * | 12/2007 |

OTHER PUBLICATIONS

Sood et al., The journal of Clinical Ivestigation, (Jan. 2010) vol. 120, No. 5, pp. 1515-1523.*
Luo et al., Cancer Letters, vol. 289 (2010), pp. 127-139.*
Jean-Philippe dales et al., International Journal of Oncology, vol. 22 (2003), pp. 391-397.*
Lin et al., J. Clin. Invest., vol. 100(8), (1997), pp. 2072-2078.*
Severine Meunier-Carpentier et al., International journal of Oncology, vol. 26, (2005), pp. 977-984.*
U.S. Appl. No. 12/021,638, filed Jan. 29, 2008, Bjergarde et al.
Nagar et al, Facile Generation of Pyridopyrazoles: Synthesis of 3-amino-4-aryl-6-(p-benzoylaminophenyl)-pyrido-[2,3-d]-1-H-pyrazoles, J. Inst. Chemists (India), 2002, 74(4), pp. 129-131.
Sennitskaya et al, English Translation of: Structural Study of Indazoles, Pyrazolo[3,4-b]pyridines and Pyrazolo[3,4-b]pyrazine Using IR Spectroscopy, Chemistry of Heterocyclic Compounds, 1977, (5), pp. 662-667.
Sennitskaya et al, Structural Study of lndazoles, Pyrazolo[3,4-b]pyridines and Pyrazolo[3,4-b]pyrazine Using IR Spectroscopy, Chemistry of Heterocyclic Compounds, 1977, (5), pp. 662-667.
Zhao et al, Regulation of the Cell Cycle by Focal Adhesion Kinase, J. Cell. Biol., 1998 (143) 7, pp. 1997-2008.
Asahara et al, Tie2 Receptor Ligands, Angiopoietin-1 and Angiopoietin-2, Modulate VEGF-Induced Postnatal Neovascularization, Circ. Res., 1998 (83) pp. 233-240.
Cary et al, Stimulation of cell migration by overexpression of focal adhesion kinase and its association with Src and Fyn, Journal of Cell Science, 1996 (109), pp. 1787-1794.
Chen et al, Association of focal adhesion kinase with its potential substrate phosphatidylinositol 3-kinase, Proc. Natl. Acad. Sci. USA, 1994 (91), pp. 10148-10152.
Davis et al, Isolation of Angiopoietin-1, a Ligand for the TIE2 Receptor, by Secretion-Trap Expression Cloning, Cell, 1996 (87) pp. 1161-1169.
De Marco et al, Lipophilicity-related inhibition of blood platelet aggregation by nipecotic acid anilides, Euro. Journal Pharma. Sciences, 2004 (22) pp. 153-164.
Dumont et al, Dominant-negative and targeted null mutations in the endothelial receptor tyrosine kinase, tek, reveal a critical role in vasculogenesis of the embryo, Genes Dev., 1994 (8) pp. 1897-1909.
Kornberg et al, Cell Adhesion or Integrin Clustering Increases Phosphorylation of a Focal Adhesion-associated Tyrosine Kinase, J. Biol. Chem., 1992 (267) 33, pp. 23439-23442.
Lee et al, Anti-Vascular Endothelial Growth Factor Treatment Augments Tumor Radiation Response under Normoxic or Hypoxic Conditions 1, Cancer Research, 2000 (60) 19 pp. 5565-5570.

(Continued)

*Primary Examiner* — D M Seaman
*Assistant Examiner* — Niloofar Rahmani
(74) *Attorney, Agent, or Firm* — Scully, Scott, Murphy & Presser, P.C.

(57) ABSTRACT

The disclosure relates to substituted pyrazolo-pyridines, compositions containing them, methods for the production thereof, and to their use as medicaments, in particular, as anticancer agents.

24 Claims, No Drawings

OTHER PUBLICATIONS

Lin et al, Antiangiogenic gene therapy targeting the endothelium-specific receptor tyrosine kinase Tie2, PNAS, 1998 (95) pp. 8829-8834.

Lin et al, Inhibition of Tumor Angiogenesis Using a Soluble Receptor Establishes a Role for Tie2 in Pathologic Vascular Growth, J. Clin. Invest., 1997 (100) 8 pp. 2072-2078.

Ling et al, Malignant Astrocytoma Cell Attachment and Migration to Various Matrix Proteins Is Differentially Sensitive to Phosphoinositide 3-OH Kinase Inhibitors, J. Cell. Biochemistry, 1999 (73), pp. 533-544.

Maisonpierre et al, Angiopoietin-2, a Natural Antagonist for Tie2 That Disrupts in vivo Angiogenesis, Science, 1997 (277) pp. 55-60.

Maung et al, Requirement for focal adhesion kinase in tumor cell adhesion, Oncogene, 1999 (18), pp. 6824-6828.

Millauer et al, Dominant-Negative Inhibition of Flk-1 Suppresses the Growth of Many Tumor Types in Vivo, Cancer Research, 1996 (56) pp. 1615-1620.

Oktay et al, Integrin-mediated Activation of Focal Adhesion Kinase Is Required for Signaling to Jun NH2-terminal Kinase and Progression through the G1 Phase of the Cell Cycle, J. Cell. Biol., 1999 (145) 7 pp. 1461-1469.

Owens et al, Overexpression of the Focal Adhesion Kinase (p125 FAK) in Invasive Human Tumors 1, Cancer Research, 1995 (55), pp. 2752-2755.

Richardson et al, A mechanism for regulation of the adhesion-associated protein tyrosine kinase pp125 FAK, Nature, 1996 (380), pp. 538-540.

Schaller et al, Autophosphorylation of the Focal Adhesion Kinase, pp125 FAK, Directs SH2-Dependent Binding of pp60src, Mol. Cell. Biol., 1994 (14), pp. 1680-1688.

Schlaepfer et al, Focal Adhesion Kinase Overexpression Enhances Ras-dependent Integrin Signaling to ERK2/Mitogen-activated Protein Kinase through Interactions with and Activation of c-Src, J. Biol. Chem., 1997 (272) 20, pp. 13189-13195.

Schlaepfer et al, Integrin-mediated signal transduction linked to Ras pathway by GRB2 binding to focal adhesion kinase, Nature, 1994 (372) 22, pp. 786-791.

Schlaepfer et al, Signaling through focal adhesion kinase, Prog. Biophy. Mol. Biol., 1999 (71), pp. 435-478.

Sieg et al, Required role of focal adhesion kinase (FAK) for integrin-stimulated cell migration, J. Cell Science, 1999 (112), pp. 2677-2691.

Strawn et.al, Flk-1 as a Target for Tumor Growth Inhibition, Cancer Research, 1996 (56) pp. 3540-3545.

Suri et al, Requisite Role of Angiopoietin-1, a Ligand for the TIE2 Receptor, during Embryonic Angiogenesis, Cell, 1996 (87) pp. 1171-1180.

Vuori et al, Induction of p130cas Signaling Complex Formation upon Integrin-Mediated Cell Adhesion: a Role for Src Family Kinases, Mol. Cell. Biol., 1996 (16) 6, pp. 2606-2613.

Wang et al, p125 focal adhesion kinase promotes malignant astrocytoma cell proliferation in vivo, J. Cell Sci., 2000 (113), pp. 4221-4230.

Weiner et al, Expression of focal adhesion kinase gene and Invasive cancer, Lancet., 1993 (342), pp. 1024-1025.

Xing et al, Direct Interaction of v-Src with the Focal Adhesion Kinase Mediated by the Src SH2 Domain, Mol. Biol. of the Cell, 1994 (5), pp. 413-421.

Xu et al, Attenuation of the Expression of the Focal Adhesion Kinase Induces Apoptosis in Tumor Cells, Cell Growth Diff., 1996 (7), pp. 413-418.

\* cited by examiner

SUBSTITUTED PYRAZOLOPYRIDINES, COMPOSITIONS CONTAINING THEM, METHOD FOR THE PRODUCTION THEREOF, AND THEIR USE

The present invention relates especially to novel chemical compounds, particularly novel substituted pyrazolopyridines, to compositions containing them and to their use as medicaments.

More particularly, and according to a first aspect, the invention relates to novel specific pyrazolopyridines with anticancer activity, via modulation of the activity of proteins, in particular kinases.

At the present time, most of the commercial compounds used in chemotherapy present considerable problems of side effects and of patient tolerance. These effects might be limited if the medicaments used act selectively on cancer cells, without touching healthy cells. One of the solutions for limiting the adverse effects of a chemotherapy may thus consist in using medicaments that act on metabolic pathways or on constituent elements of these pathways, expressed predominantly in cancer cells, and which are expressed little or not at all in healthy cells.

Protein kinases are a family of enzymes that catalyse the phosphorylation of hydroxyl groups of specific residues of proteins, such as tyrosine, serine or threonine residues. Such phosphorylations may greatly modify the function of the proteins; thus, protein kinases play an important role in regulating a wide variety of cell processes including, especially, metabolism, cell proliferation, cell differentiation, cell migration and cell survival. Among the various cellular functions in which the activity of a protein kinase is involved, certain processes represent attractive targets for treating cancer cells and also other diseases.

Thus, one of the objects of the present invention is to propose compositions with anticancer activity, by acting in particular with respect to kinases. Among the kinases for which modulation of the activity is desired, FAK, KDR and Tie2 are preferred.

These products correspond to formula (I) below:

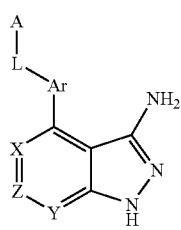

Formula (I)

in which:
1) A and Ar are independently selected from the group consisting of: aryl, heteroaryl, substituted aryl, substituted heteroaryl, cycloalkyl, substituted cycloalkyl, heterocyclyl, substituted heterocyclyl;
2) L is selected from the group consisting of: bond, CO, NH, CO—NH, NH—CO, NH—SO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH;
3) one from among X, Y and Z is chosen from N and NO, and two others from among Z, Y and X are C(R5) and C(R6);
4) R5 and R6 are independently selected from the group consisting of: H, halogen, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3); in which each R2, R3 and R4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, substituted alkynyl; in which R2 and R3 may be linked together to form a 4- to 8-membered ring containing from 1 to 3 hetero atoms chosen from O, N and S.

In the products of formula (I), Ar-L-A is advantageously:

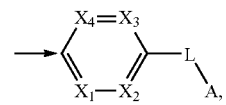

in which each X1, X2, X3 and X4 is independently chosen from N and C—R11, with R11 having the same definition as R5 defined above.

Ar-L-A is advantageously:

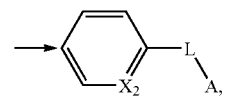

in which X2 is chosen from N, C—CH$_3$, CF and CH.

Substituents R11 selected from the group consisting of H, F, Cl, methyl, NH$_2$, OCF$_3$ and CONH$_2$ are preferred.

Preferred substituents R5 and R6 are independently selected from H, halogen, OMe and methyl.

R5 and R6 are advantageously chosen from H and F.

R5 and R6 are preferentially H.

Preferred substituents L-A are advantageously chosen from NH—CO—NH-A and NH—SO$_2$-A.

A combination L-A that is particularly effective is obtained when L-A is NH—CO—NH-A.

Products in accordance with the invention preferably have a substituent A that is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted.

More preferably, A is chosen from phenyl, pyrazolyl and isoxazolyl; optionally substituted.

The substituent A is very advantageously substituted with a substituent selected from a first group consisting of (C1-C6)alkyl, (C1-C6)haloalkyl, (C2-C6)alkylene, (C2-C6)alkynyl, aryl, halogen, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen and O—(C1-C3)alkyl.

The substituent A is preferentially substituted with a substituent selected from a second group consisting of F, Cl, Br, I, OH, SH, SO$_3$M, COOM, CN, NO$_2$, CON(R8)(R9), N(R8)

CO(R9), (C1-C3)alkyl-OH, (C1-C3)alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)alkyl-OH, (C1-C3)alkyl-NH$_2$, (C1-C3)alkyl-COOM, (C1-C3)alkyl-SO$_3$M; in which, when R8 and R9 are simultaneously other than H, they may be bonded to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

Substituents A that are particularly preferred are chosen from phenyl and isoxazolyl; the said substituents A possibly being substituted with halogen, (C1-C4)alkyl, (C1-C3)haloalkyl, O—(C1-C4)alkyl, S—(C1-C4)alkyl, O—(C1-C4)haloalkyl and S—(C1-C4)haloalkyl. When A is disubstituted, the two substituents of A may form a 5- to 7-membered ring containing from 0 to 3 hetero atoms.

A is advantageously substituted with one or more substituents, which may be identical or different, independently selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9), (C1-C6)alkyl, (C2-C6)alkylene, (C2-C6)alkynyl, aryl, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen, O—(C1-C3)alkyl; in which R8 and R9 are independently chosen from H, (C1-C3)alkyl, (C1-C3)alkyl-OH, (C1-C3)alkyl-NH$_2$, (C1-C3)alkyl-COOM and (C1-C3)alkylSO$_3$M; in which, when R8 and R9 are simultaneously other than H, they may be linked to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

According to one preferred embodiment, A is advantageously 2-fluoro-5-trifluoromethylphenyl or 2-methoxy-5-trifluoromethylphenyl.

Products in accordance with the invention may be chosen from:
1-[4-(3-Amino-1H-pyrazolo[3,4-b]pyrid-4-yl)phenyl]-3-(2-fluoro-5-trifluoromethyl-phenyl)urea,
1-[5-(3-Amino-1H-pyrazolo[3,4-b]pyrid-4-yl)pyrid-2-yl]-3-(2-fluoro-5-trifluoro-methylphenyl)urea,
1-[4-(3-Amino-1H-pyrazolo[3,4-b]pyrid-4-yl)phenyl]-3-(2-methoxy-5-trifluoro-methylphenyl)urea,
1-[5-(3-Amino-1H-pyrazolo[3,4-b]pyrid-4-yl)pyrid-2-yl]-3-(2-methoxy-5-trifluoro-methylphenyl)urea,
1-[4-(3-Amino-1H-pyrazolo[3,4-b]pyrid-4-yl)phenyl]-3-(2-methylcarbonylamino-5-trifluoromethylphenyl)urea,
1-[5-(3-Amino-1H-pyrazolo[3,4-b]pyrid-4-yl)pyrid-2-yl]-3-(2-methylcarbonylamino-5-trifluoromethylphenyl)urea,
1-[4-(3-Amino-1H-pyrazolo[3,4-b]pyrid-4-yl)phenyl]-3-(2-ethoxy-5-trifluoro-methylphenyl)urea,
1-[4-(3-Amino-1H-pyrazolo[3,4-b]pyrid-4-yl)phenyl]-3-(2-fluoro-5-methyl-phenyl)urea,
3-{3-[4-(3-Amino-1H-pyrazolo[3,4-b]pyrid-4-yl)phenyl]ureido}-4-methoxybenzoic acid,
1-[4-(3-Amino-1H-pyrazolo[3,4-b]pyrid-4-yl)phenyl]-3-(2-hydroxy-5-trifluoro-methylphenyl)urea,
1-[4-(3-Amino-1H-pyrazolo[3,4-b]pyrid-4-yl)phenyl]-3-(3,4-dimethylphenyl)urea,
1-[4-(3-Amino-1H-pyrazolo[3,4-b]pyrid-4-yl)phenyl]-3-(2-methoxy-5-tert-butyl-phenyl)urea,
1-[4-(3-Amino-1H-pyrazolo[3,4-b]pyrid-4-yl)phenyl]-3-(3-trifluoromethyl-4-methylphenyl)urea,
1-[4-(3-Amino-1H-pyrazolo[3,4-b]pyrid-4-yl)phenyl]-3-(3-chloro-4-methyl-phenyl)urea,
1-[4-(3-Amino-1H-pyrazolo[3,4-b]pyrid-4-yl)phenyl]-3-(3-ethylphenyl)urea,
1-[4-(3-Amino-1H-pyrazolo[3,4-b]pyrid-4-yl)phenyl]-3-1,3-benzodioxol-5-yl-urea,
1-[4-(3-Amino-1H-pyrazolo[3,4-b]pyrid-4-yl)phenyl]-3-(3-chloro-4-methoxy-phenyl)urea,
1-[4-(3-Amino-1H-pyrazolo[3,4-b]pyrid-4-yl)phenyl]-3-(2-methoxy-5-chloro-phenyl)urea,
1-[4-(3-Amino-1H-pyrazolo[3,4-b]pyrid-4-yl)phenyl]-3-(2-ethoxyphenyl)urea,
1-[4-(3-Amino-1H-pyrazolo[3,4-b]pyrid-4-yl)phenyl]-3-(2-methoxy-5-methyl-phenyl)urea,
N-[4-(3-Amino-1H-pyrazolo[3,4-b]pyrid-4-yl)phenyl]-2,3-dichlorobenzene-sulfonamide.

Other products in accordance with the invention may be chosen from:
1-[4-(3-Amino-1H-pyrazolo[4,3-c]pyrid-4-yl)phenyl]-3-(2-fluoro-5-trifluoro-methylphenyl)urea,
1-[5-(3-Amino-1H-pyrazolo[4,3-c]pyrid-4-yl)pyrid-2-yl]-3-(2-fluoro-5-trifluoro-methylphenyl)urea,
1-[4-(3-Amino-1H-pyrazolo[4,3-c]pyrid-4-yl)phenyl]-3-(phenyl)urea,
1-[5-(3-Amino-1H-pyrazolo[4,3-c]pyrid-4-yl)pyrid-2-yl]-3-(2-methoxy-5-trifluoro-methylphenyl)urea,
1-[4-(3-Amino-1H-pyrazolo[4,3-c]pyrid-4-yl)phenyl]-3-(2-methoxy-5-trifluoro-methylphenyl)urea,
1-[4-(3-Amino-1H-pyrazolo[4,3-c]pyrid-4-yl)phenyl]-3-(2-methylcarbonylamino-5-trifluoromethylphenyl)urea,
1-[4-(3-Amino-1H-pyrazolo[4,3-c]pyrid-4-yl)phenyl]-3-(2-fluoro-5-methyl-phenyl)urea,
1-[4-(3-Amino-1H-pyrazolo[4,3-c]pyrid-4-yl)phenyl]-3-(2,4-dimethoxyphenyl)urea,
N-[4-(3-Amino-1H-pyrazolo[4,3-c]pyrid-4-yl)phenyl]-2,3-dichlorobenzenesulfonamide,
1-[4-(3-Amino-1H-pyrazolo[4,3-c]pyrid-4-yl)phenyl]-3-(2-methoxy-5-tert-butyl-phenyl)urea,
1-[4-(3-Amino-1H-pyrazolo[4,3-c]pyrid-4-yl)phenyl]-3-(3,4-dimethylphenyl)urea,
1-[4-(3-Amino-1H-pyrazolo[4,3-c]pyrid-4-yl)phenyl]-3-(3-trifluoromethyl-4-methylphenyl)urea,
1-[4-(3-Amino-1H-pyrazolo[4,3-c]pyrid-4-yl)phenyl]-3-(2,5-difluorophenyl)urea,
1-[4-(3-Amino-1H-pyrazolo[4,3-c]pyrid-4-yl)phenyl]-3-(3-chloro-4-methyl-phenyl)urea,
1-[4-(3-Amino-1H-pyrazolo[4,3-c]pyrid-4-yl)phenyl]-3-(2-methyl-5-fluorophenyl)-urea,
1-[4-(3-Amino-1H-pyrazolo[4,3-c]pyrid-4-yl)phenyl]-3-(2,4-dimethoxy-5-chlorophenyl)urea,
1-[4-(3-Amino-1H-pyrazolo[4,3-c]pyrid-4-yl)phenyl]-3-(3-trifluoromethyl-sulfanylphenyl)urea.

Other products in accordance with the invention may be chosen from:
1-[4-(3-Amino-1H-pyrazolo[3,4-c]pyrid-4-yl)phenyl]-3-(2-fluoro-5-trifluoro-methylphenyl)urea,
1-[4-(3-Amino-1H-pyrazolo[3,4-c]pyrid-4-yl)phenyl]-3-(2-methoxy-5-trifluoro-methylphenyl)urea,
N-[4-(3-Amino-1H-pyrazolo[3,4-c]pyrid-4-yl)phenyl]-2,3-dichlorobenzene-sulfonamide.

A product in accordance with the invention may be:
in achiral form, or
in racemic form, or
enriched in one stereoisomer, or
enriched in one enantiomer;
may be optionally salified, may be optionally hydrated, and may be optionally solvated.

A product in accordance with the invention may be used for the manufacture of a medicament that is useful for treating a pathological condition, in particular a cancer.

According to a second aspect, the invention relates to a medicament, comprising a product of formula (I) according to its first aspect, or an addition salt of this compound with a pharmaceutically acceptable acid, or alternatively a hydrate or a solvate of the product of formula (I).

According to a third aspect, the invention relates to a pharmaceutical composition comprising a product according to its first or its second aspect, in combination with a pharmaceutically acceptable excipient.

According to a fourth aspect, the invention relates to the use of a product according to one of the other aspects of the invention, as an inhibitor of a reaction catalysed by a kinase. Among the kinases, FAK, KDR and Tie2 are preferred.

The present invention also relates to therapeutic compositions comprising a product according to the invention, in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route usually being preferred.

The administered dose of the compounds of the invention will be adapted by the practitioner as a function of the route of administration to the patient and of the patient's condition.

The compounds of the present invention may be administered alone or as a mixture with other anticancer agents. Among the possible combinations that may be mentioned are:
alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine
platinum derivatives such as, especially, cisplatin, carboplatin or oxaliplatin
antibiotics such as, especially, bleomycin, mitomycin or dactinomycin antimicrotubule agents such as, especially, vinblastine, vincristine, vindesine, vinorelbine and taxoids (paclitaxel and docetaxel)
anthracyclines such as, especially, doxorubicin, daunorubicin, idarubicin, epirubicin, mitoxantrone and losoxantrone
group I and II topoisomerase inhibitors such as etoposide, teniposide, amsacrine, irinotecan, topotecan and tomudex
fluoropyrimidines such as 5-fluorouracil, UFT and floxuridine
cytidine analogues such as 5-azacytidine, cytarabine, gemcitabine, 6-mercaptomurine and 6-thioguanine
adenosine analogues such as pentostatin, cytarabine or fludarabine phosphate
methotrexate and folinic acid
various enzymes and compounds such as L-asparaginase, hydroxyurea, trans-retinoic acid, suramine, dexrazoxane, amifostine and herceptin, and also oestrogen-based and androgenic hormones
antivascular agents such as combretastatin or colchicine derivatives and prodrugs thereof.

It is also possible to combine the compounds of the present invention with a radiation treatment. These treatments may be administered simultaneously, separately or sequentially. The treatment will be adapted by the practitioner as a function of the patient to be treated.

The products of the invention are useful as inhibitors of a reaction catalysed by a kinase. FAK, KDR and Tie2 are kinases for which the products of the invention will be particularly useful as inhibitors.

The reasons for which these kinases are chosen are given below:
FAK

FAK is a cytoplasmic tyrosine kinase that plays an important role in transducing the signal transmitted by the integrins, a family of heterodimeric cellular adhesion receptors. FAK and the integrins are colocated in perimembrane structures known as adhesion plaques. It has been shown in many cell types that the activation of FAK and its phosphorylation on tyrosine residues and in particular its autophosphorylation on tyrosine 397 were dependent on the binding of integrins to their extracellular ligands and thus induced during cellular adhesion [Kornberg L, et al. J. Biol. Chem. 267(33): 23439-442 (1992)]. Autophosphorylation on tyrosine 397 of FAK represents a binding site for another tyrosine kinase, Src, via its SH2 domain [Schaller et al. Mol. Cell. Biol. 14: 1680-1688 1994; Xing et al. Mol. Cell. Biol. 5: 413-421 1994]. Src may then phosphorylate FAK on tyrosine 925, thus recruiting the adapter protein Grb2 and inducing in certain cells activation of the ras and MAP kinase pathway involved in controlling cell proliferation [Schlaepfer et al. Nature; 372: 786-791 1994; Schlaepfer et al. Prog. Biophy. Mol. Biol. 71: 435-478 1999; Schlaepfer and Hunter, J. Biol. Chem. 272: 13189-13195 1997]. The activation of FAK may also induce the jun NH2-terminal kinase (JNK) signalling pathway and result in the progression of cells towards the G1 phase of the cell cycle [Oktay et al., J. Cell. Biol. 145: 1461-1469 1999]. Phosphatidylinositol-3-OH kinase (PI3-kinase) also binds to FAK on tyrosine 397 and this interaction might be necessary for activating PI3-kinase [Chen and Guan, Proc. Nat. Acad. Sci. USA. 91: 10148-10152 1994; Ling et al. J. Cell. Biochem. 73: 533-544 1999]. The FAK/Src complex phosphorylates various substrates, for instance paxillin and p130CAS in fibroblasts [Vuori et al. Mol. Cell. Biol. 16: 2606-2613 1996].

The results of numerous studies support the hypothesis that FAK inhibitors might be useful in treating cancer. Studies have suggested that FAK might play an important role in cell proliferation and/or survival in vitro. For example, in CHO cells, some authors have demonstrated that the overexpression of p125FAK leads to an acceleration of the transition G1 to S, suggesting that p125FAK promotes cell proliferation [Zhao J.-H et al. J. Cell Biol. 143: 1997-2008 1998]. Other authors have shown that tumour cells treated with FAK antisense oligonucleotides lose their adhesion and enter into apoptosis (Xu et al., Cell Growth Differ. 4: 413-418 1996). It has also been demonstrated that FAK promotes the migration of cells in vitro. Thus, fibroblasts that are deficient for FAK expression (FAK "knockout" mice) show a rounded morphology and deficiencies in cellular migration in response to chemotactic signals, and these defects are eliminated by re-expression of FAK [D J. Sieg et al., J. Cell Science. 112: 2677-91 1999]. Overexpression of the C-terminal domain of FAK (FRNK) blocks the stretching of adherent cells and reduces cell migration in vitro [Richardson A. and Parsons J. T. Nature. 380: 538-540 1996]. Overexpression of FAK in CHO or COS cells or in human astrocytoma cells promotes migration of the cells. The involvement of FAK in promotion of the proliferation and migration of cells in many cell types in vitro suggests the potential role of FAK in neoplastic processes. A recent study has effectively demonstrated the increase in the proliferation of tumour cells in vivo after inducing the expression of FAK in human astrocytoma cells [Cary L. A. et al. J. Cell Sci. 109: 1787-94 1996; Wang D et al. J. Cell Sci. 113: 4221-4230 2000]. Furthermore, immunohistochemical studies of human biopsies have demonstrated that FAK was overexpressed in prostate cancer, breast cancer, thyroid cancer, colon cancer, melanoma, brain cancer and lung cancer, the level of expression of FAK being directly correlated to the tumours showing the most aggressive phenotype [Weiner T M, et al. Lancet. 342 (8878): 1024-1025 1993; Owens et al. Cancer Research. 55: 2752-2755 1995; Maung K. et al. Oncogene 18: 6824-6828 1999; Wang D et al. J. Cell Sci. 113: 4221-4230 2000].

KDR

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., *Cancer Research*, 1996, vol. 56, p. 3540-3545). This process has especially been demonstrated using VEGF-R2 mutants (Millauer et al., *Cancer Research*, 1996, vol. 56, p. 1615-1620). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. *Cancer Research*, 2000, vol. 60, p. 5565-5570).

Tie2

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signalling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts.

Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile haemoangioma and cancers).

DEFINITIONS

The term "halogen" refers to an element chosen from F, Cl, Br and I.

The term "alkyl" refers to a linear or branched saturated hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkylene" refers to a linear or branched hydrocarbon-based substituent containing one or more unsaturations, and containing from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkylene substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 hetero atoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "hetero atom" refers herein to an at least divalent atom other than carbon. N; O; S; and Se are examples of hetero atoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopenta-dienyl; cyclohexyl; cyclohexenyl; cycloheptyl; bicyclo[2.2.1]heptyl; cyclooctyl; bicyclo[2.2.2]octyl; adamantyl; and perhydronapthyl are examples of cycloalkyl substituents.

The term "heterocyclyl" refers to a saturated or partially unsaturated cyclic hydrocarbon-based substituent containing from 1 to 13 carbon atoms and from 1 to 4 hetero atoms. Preferably, the saturated or partially unsaturated cyclic hydrocarbon-based substituent will be monocyclic and will contain 4 or 5 carbon atoms and 1 to 3 hetero atoms.

The term "substituted" refers to one or more substituents other than H, for example halogen; alkyl; aryl; heteroaryl, cycloalkyl; heterocyclyl; alkylene; alkynyl; OH; O-alkyl; O-alkylene; O-aryl; O-heteroaryl; NH$_2$; NH-alkyl; NH-aryl; NH-heteroaryl; N-alkyl-alkyl'; SH; S-alkyl; S-aryl; S(O$_2$)H; S(O$_2$)-alkyl; S(O$_2$)-aryl; SO$_3$H; SO$_3$-alkyl; SO$_3$-aryl; CHO; C(O)-alkyl; C(O)-aryl; C(O)OH; C(O)O-alkyl; C(O)O-aryl; OC(O)-alkyl; OC(O)-aryl; C(O)NH$_2$; C(O)NH-alkyl; C(O) NH-aryl; NHCHO; NHC(O)-alkyl; NHC(O)-aryl; NH-cycloalkyl; NH-heterocyclyl, CONH-heterocyclyl, CO-heteroaryl, CO-heterocyclyl NHCO-heteroaryl, NHCO-heterocyclyl, NHCONH-alkyl.

A subject of the present invention is also the process for preparing the products of formula (I).

The products according to the invention may be prepared using conventional methods of organic chemistry. Scheme 1 below illustrates the method used for the preparation of Example 1 concerning the pyrazolo[3,4-b]pyridines. In this respect, it cannot constitute a limitation of the scope of the invention, as regards the methods for preparing the claimed compounds.

Scheme 1:

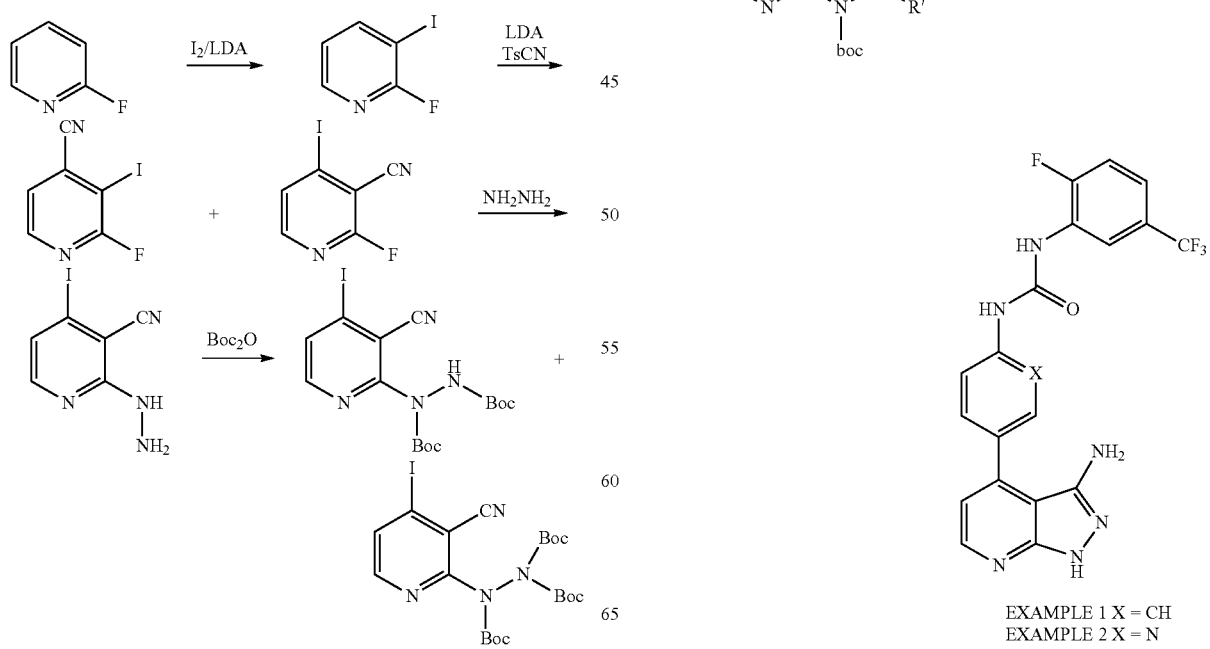

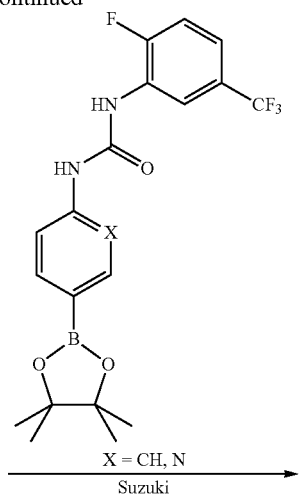

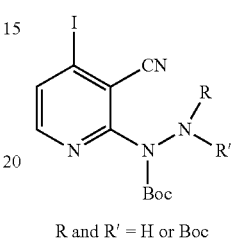

EXAMPLE 1 X = CH
EXAMPLE 2 X = N

-continued
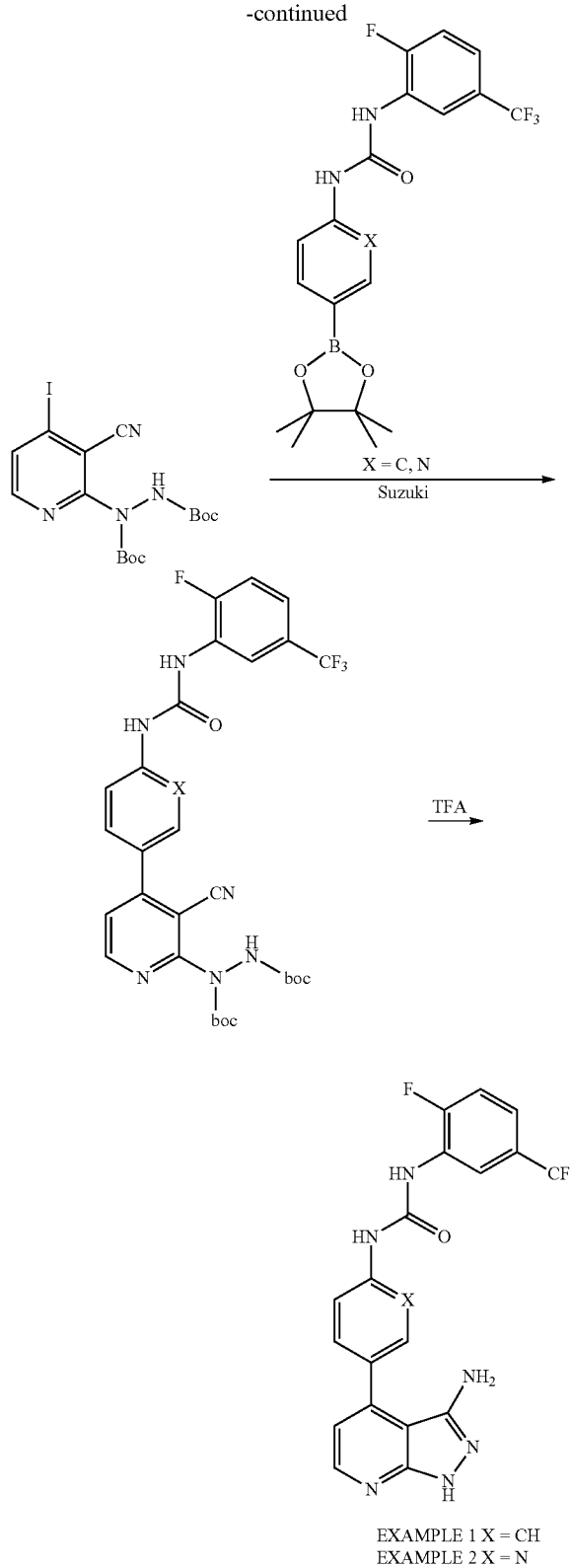
EXAMPLE 1 X = CH
EXAMPLE 2 X = N
Scheme 2 below illustrates the method used for the preparation of the examples concerning the pyrazolo[4,3-c]pyridines. In this respect, it cannot constitute a limitation of the scope of the invention, as regards the methods for preparing the claimed compounds.
Scheme 2:
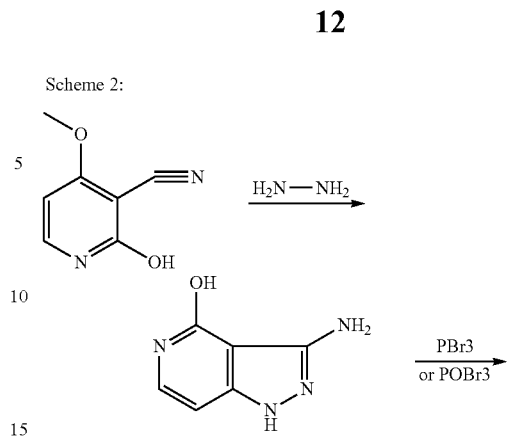
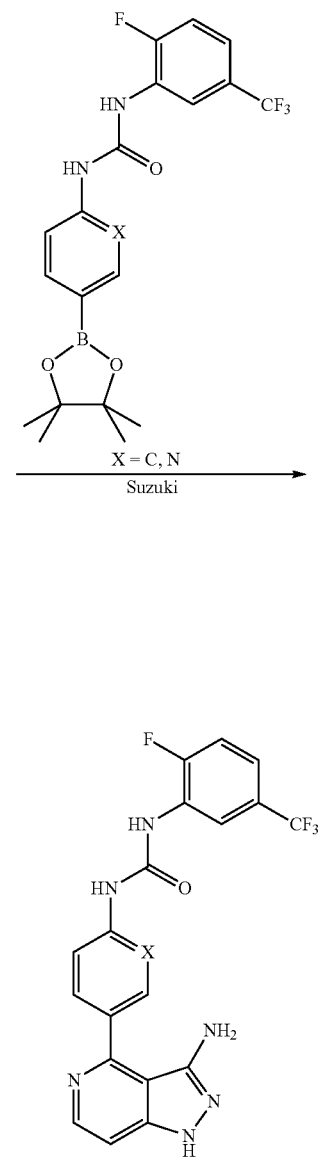

Scheme 3:
Process for preparing pyrazolo[3,4-c]pyridines (non-limiting):
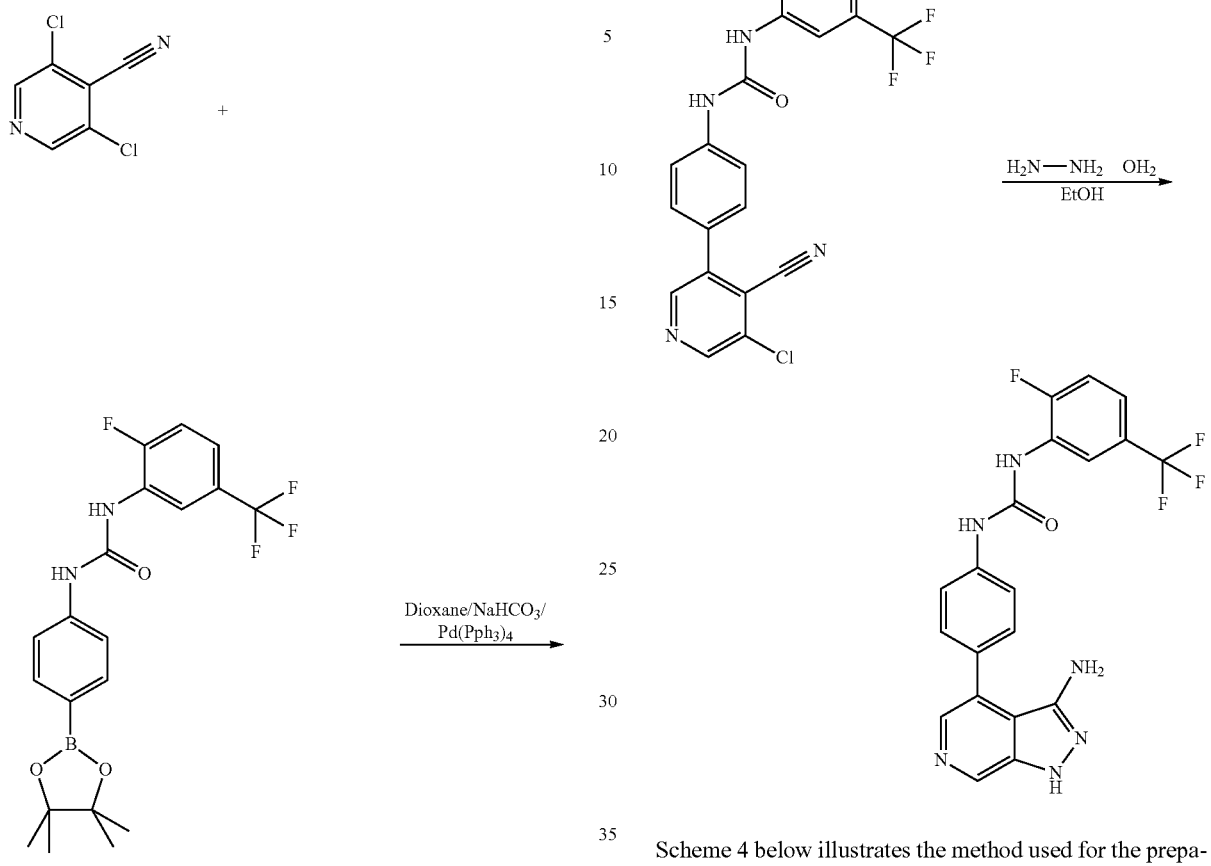
Scheme 4 below illustrates the method used for the preparation of the examples concerning the chains of boronate derivatives.
Scheme 4:
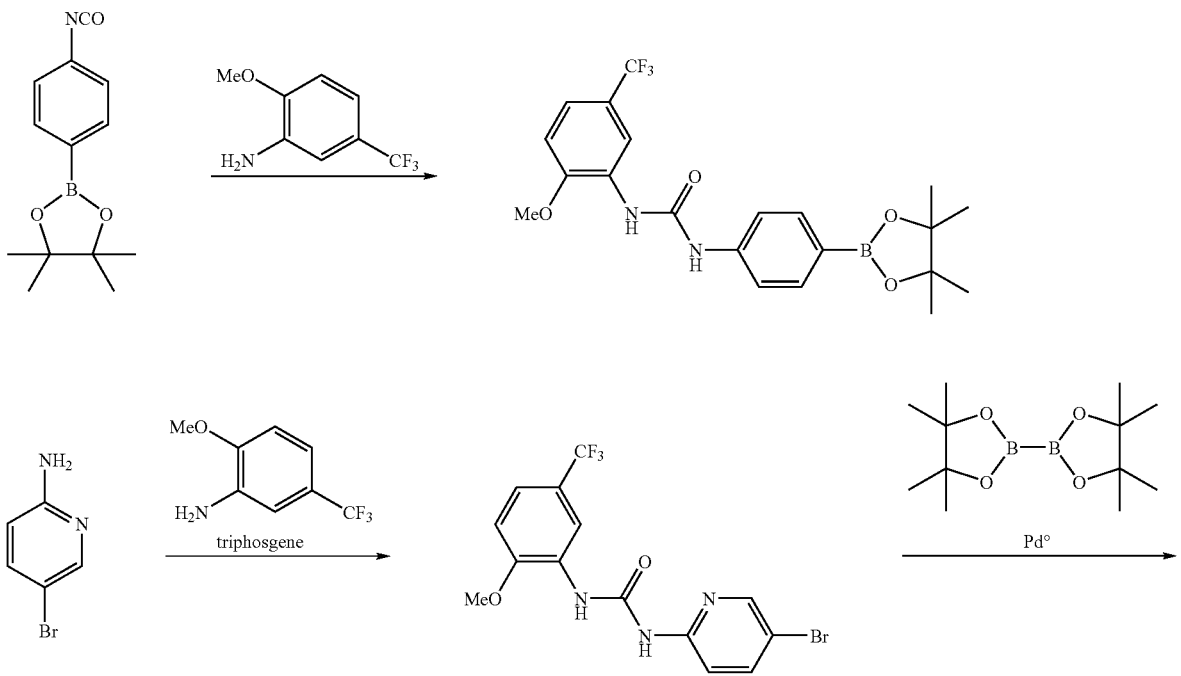

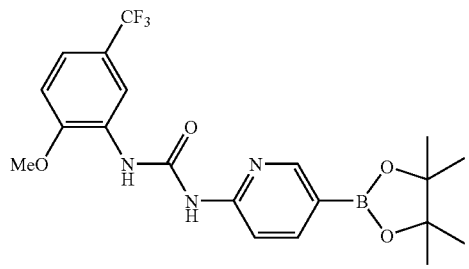

Scheme 5 below illustrates the method used for the preparation of 4-iodo-1H-pyrazolo[3,4-b]pyrid-3-ylamine.

Scheme 5:

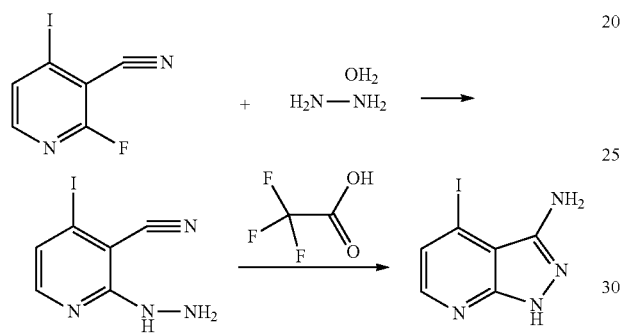

Scheme 6 below illustrates the method used for the preparation of urea derivatives of 4-bromo-1H-pyrazolo[4,3-c]pyrid-3-ylamine.

Scheme 6:

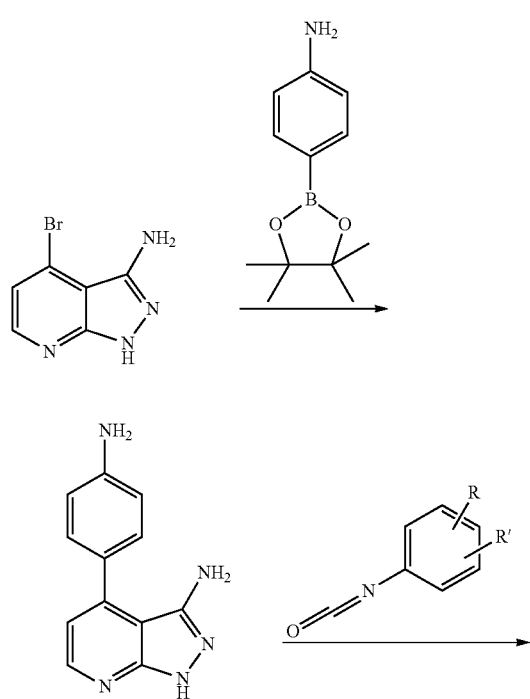

-continued

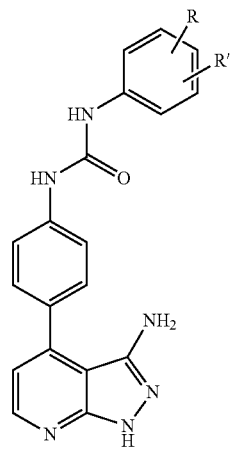

Scheme 7 below illustrates the alternative method used for the preparation of the examples concerning the pyrazolo[4,3-c]pyridines.

Scheme 7:

-continued

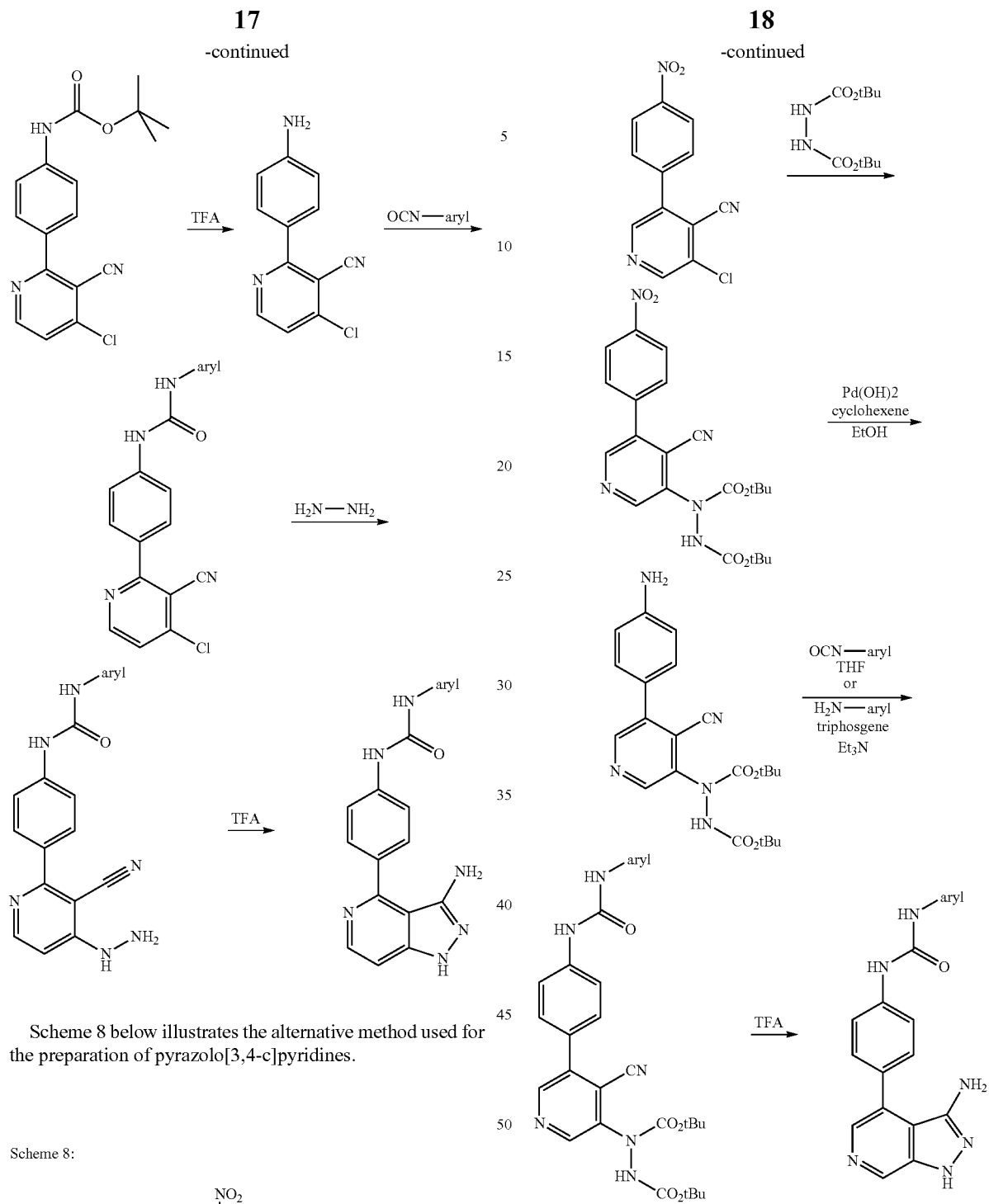

Scheme 8 below illustrates the alternative method used for the preparation of pyrazolo[3,4-c]pyridines.

Scheme 8:

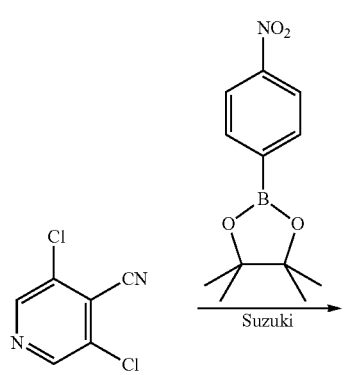

It is understood by a person skilled in the art that, for the implementation of the processes according to the invention described above, it may be necessary to introduce protecting groups for the amino, carboxyl and alcohol functions in order to avoid side reactions. These groups are those that can be removed without affecting the rest of the molecule. As examples of protecting groups for the amino function, mention may be made of tert-butyl carbamate, which may be regenerated using trifluoroacetic acid or iodotrimethylsilane, and acetyl, which may be regenerated in acidic medium (for example hydrochloric acid). As protecting groups for the carboxyl function, mention may be made of esters (for example methoxymethyl ester or benzyl ester). As protecting groups for the alcohol function, mention may be made of esters (for example benzoyl ester), which may be regenerated in acidic medium or by catalytic hydrogenation. Other protecting groups that may be used are described by T. W. Greene et al. in Protective Groups in Organic Synthesis, third edition, 1999, Wiley-Interscience.

Another subject of the present invention relates to the compounds of general formula (II):

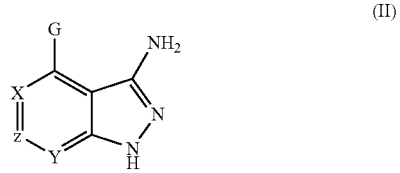

(II)

in which X, Y, Z are as defined above and G is a halogen atom that is suitable in the Suzuki coupling reaction, as intermediate products for the preparation of the products of general formula (I) as defined in Claim 1.

Another subject of the present invention relates to the compounds of general formula (III):

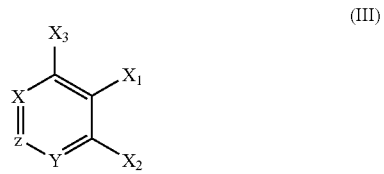

(III)

in which:
X, Y and Z are as defined above,
$X_3$ is Ar-L-A in which Ar, L and A are as defined above, or Ar-L in which Ar is as defined above and L is $NH_2$ or $NO_2$,
$X_1$ and $X_2$ are different and chosen independently from CN, Cl, —NH—$NH_2$, —N(Boc)-NH(Boc) and —N(Boc)-N(Boc)$_2$, as intermediate products for the preparation of the products of general formula (I) as defined in Claim 1.

The compounds of formula (I) are isolated and may be purified by means of the usual known methods, for example by crystallization, chromatography or extraction.

The enantiomers and diastereoisomers of the compounds of formula (I) also form part of the invention.

The compounds of formula (I) comprising a basic residue may be optionally converted into addition salts with a mineral or organic acid, via the action of such an acid in a solvent, for example an organic solvent such as an alcohol, a ketone, an ether or a chlorinated solvent.

The compounds of formula (I) comprising an acid residue may be optionally converted into metal salts or into addition salts with nitrogen bases according to methods that are known per se. These salts may be obtained via the action of a metallic base (for example an alkali metal or alkaline-earth metal base), ammonia, an amine or an amine salt on a compound of formula (I), in a solvent. The salt formed is separated out via the usual methods.

These salts also form part of the invention.

When a product according to the invention contains at least one free basic function, pharmaceutically acceptable salts may be prepared by reaction between the said product and a mineral or organic acid. Pharmaceutically acceptable salts include chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, p-toluene-sulfonate, propanesulfonates, xylenesulfonates, salicylates, cinnamates, glutamates, aspartates, glucuronates and galacturonates.

When a product according to the invention contains at least one free acid function, pharmaceutically acceptable salts may be prepared by reaction between the said product and a mineral or organic base. Pharmaceutically acceptable bases include hydroxides of cations of alkali metals or alkaline-earth metals such as Li, Na, K, Mg or Ca, and basic amino compounds such as ammonia, arginine, histidine, piperidine, morpholine, piperazine or triethylamine.

The invention is also described by the examples that follow, which are given as illustrations of the invention.

The LC/MS analyses were performed on an LCT Micromass machine connected to an HP 1100 machine. The abundance of the products was measured using an HP G1315A diode array detector over a wavelength range of 200-600 nm and a Sedex 65 light scattering detector. The mass spectra were acquired over a range from 180 to 800. The data were analysed using the Micromass MassLynx software. The separation was performed on a Hypersil BDS C18 3 µm (50×4.6 mm) column, eluting with a linear gradient of 5% to 90% acetonitrile containing 0.05% (v/v) of trifluoroacetic acid (TFA) in water containing 0.05% (v/v) of TFA, over 3.5 minutes at a flow rate of 1 ml/minute. The total analysis time, including the column reequilibration period, is 7 minutes.

The mass spectra were acquired in electrospray (ES$^+$) mode on a Platform II (Micromass) machine. The main ions observed are described.

The melting points were measured by capillary, on a Mettler FP62 machine, over the range 30° C. to 300° C., with a temperature rise of 2° C. per minute.

Purification by LC/MS:

The products may be purified by LC/MS using a Waters FractionsLynx system composed of a Waters 600 gradient pump, a Waters 515 regeneration pump, a Waters Reagent Manager dilution pump, a Waters 2700 auto-injector, two Rheodyne LabPro valves, a Waters 996 diode array detector, a Waters ZMD mass spectrometer and a Gilson 204 fraction collector. The system was controlled by the Waters FractionLynx software. The separation was performed alternately on two Waters Symmetry ($C_{18}$, 5 µM, 19×50 mm, catalogue reference 186000210) columns, one column undergoing regeneration with a 95/5 (v/v) water/acetonitrile mixture containing 0.07% (v/v) of trifluoroacetic acid, while the other column was being used for separation. The columns were eluted using a linear gradient of 5% to 95% acetonitrile containing 0.07% (v/v) of trifluoroacetic acid in water containing 0.07% (v/v) of trifluoroacetic acid, at a flow rate of 10 ml/minute. On leaving the separation column, one thousandth of the effluent is separated out using an LC Packing Accurate machine, diluted with methanol at a flow rate of 0.5 ml/minute and conveyed to the detectors, in a proportion of 75% to the diode array detector and the remaining 25% to the mass spectrometer. The rest of the effluent (999/1000) is conveyed to the fraction collector, where the flow is discarded if the mass of the expected product is not detected by the FractionLynx software. The molecular formulae of the expected products are supplied to the FractionLynx software, which triggers the collection of the product when the mass signal detected corresponds to the [M+H]+ ion and/or to the [M+Na]+ ion. In certain cases, depending on the analytical LC/MS results, when an intense ion corresponding to [M+2H]++ was detected, the value corresponding to half the calculated molecular mass (MW/2) is also supplied to the FractionLynx software. Under these conditions, collection is also triggered when the mass signal of the [M+2H]++ and/or [M+Na+H]++ ion is detected. The products were collected in tared glass tubes. After collection, the solvents were evaporated off, in a Savant AES 2000 or Genevac HT8 centrifugal evaporator and the masses of the products were determined by weighing the tubes after evaporation of the solvents.

EXAMPLE 1

1-[4-(3-Amino-1H-pyrazolo[3,4-b]pyrid-4-yl)phenyl]-3-(2-fluoro-5-trifluoromethylphenyl)urea

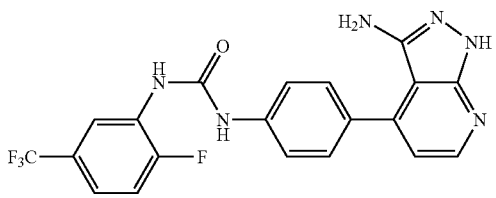

2-fluoro-3-iodopyridine

To a solution of 0.103 mol of LDA in 200 mL of THF at −75° C. are added 10 g of 2-fluoropyridine in 50 mL of THF. The yellow solution is stirred for 3 hours at −75° C., followed by addition of 26.2 g of iodine in 80 mL of THF. The reaction mixture is stirred for 1.5 hours at −75° C., followed by addition of 50 mL of water at this temperature. The temperature is allowed to rise, and a further 100 mL of water are added at 0° C. The suspension is decolourized by adding sodium thiosulfate. The mixture is extracted with diethyl ether. The organic phase is dried over magnesium sulfate and then concentrated under reduced pressure. The oily residue is purified on silica Si60 (40-63 μm) (95/5 cyclohexane/diethyl ether). The product obtained is taken up in diethyl ether and an insoluble beige-coloured material is removed by filtration by suction. After drying under vacuum, 10.21 g of a white powder of 2-fluoro-3-iodopyridine are obtained.

MS spectrum (ES+): m/z=224 [MH+]

2-Fluoro-4-iodonicotinonitrile

To a solution of 21.5 mmol of LDA in 20 mL of THF at −75° C. are added 4.8 g of 2-fluoro-3-iodopyridine in 20 mL of THF. The yellow solution is stirred for one hour 10 minutes at −75° C., and 3.9 g of para-toluenesulfonyl cyanide in 20 mL of THF are then added at this temperature. The reaction mixture is stirred for 2 hours at −75° C., followed by addition of 20 mL of water at this temperature. The temperature is allowed to rise, and a further 40 mL of water are then added at 0° C. The mixture is extracted with diethyl ether. The organic phase is dried over magnesium sulfate and then concentrated under reduced pressure. The brown resin obtained is purified on silica Si60 (40-63 μm) (8/2 cyclohexane/diethyl ether). A fraction of 667 mg of a yellow powder of 2-fluoro-4-iodonicotinonitrile and a second fraction of 2.1 g of a pale yellow powder of 2-fluoro-3-iodoisonicotinonitrile are obtained.

MS spectrum (ES+): m/z=249 [MH+]

2-Hydrazino-4-iodonicotinonitrile

To a solution of 1.2 g of 2-fluoro-4-iodonicotinonitrile in 20 mL of MeOH at 20° C. are added 2.4 mL of hydrazine hydrate. The yellow suspension is stirred for 20 minutes at 20° C. and is then filtered. The precipitate is washed with methanol to give, after drying under vacuum, 947 mg of a white powder of 2-hydrazino-4-iodonicotinonitrile.

MS spectrum (ES+): m/z=261 [MH+]

Di-tert-butyl (3-cyano-4-iodopyrid-2-yl)hydrazinedicarboxylate and tri-tert-butyl N,N',N'-(3-cyano-4-iodopyrid-2-yl)hydrazinetricarboxylate To a mixture of 234 mg of 2-hydrazino-4-iodonicotinonitrile, 27.5 mg of N,N-dimethyaminopyridine and 0.316 mL of triethylamine in 11 mL of dichloromethane at 4° C. are added 492 mg of di-tert-butyl dicarbonate in 5 mL of dichloromethane. The reaction is stirred for 30 minutes at 4° C., the temperature is then allowed to rise to 20° C. and the mixture is stirred for 5 hours. Water is added and the mixture is extracted with ethyl acetate. The organic phase is dried over magnesium sulfate and then concentrated under reduced pressure. The oily yellow residue is purified on a prepacked Biotage KP-Sil column of 60 Å SiO₂ 32-63 μm (eluent: 99.5/0.5 and then 99/1 dichloromethane/methanol) to give two major fractions, a first fraction of 110 mg of a yellow powder of tri-tert-butyl N,N',N'-(3-cyano-4-iodopyrid-2-yl)hydrazinetricarboxylate (MS spectrum (ES+): m/z=561 [MH+]) and a second fraction of 202 mg of a pale yellow oil containing di-tert-butyl (3-cyano-4-iodopyrid-2-yl)hydrazinedicarboxylate. This yellow oil is re-purified on a prepacked Biotage KP-Sil column of 60 Å SiO₂ 32-63 μm (eluent: 95/5 and then 9/1 cyclohexane/ethyl acetate) to give 114 mg of a beige-coloured powder of di-tert-butyl (3-cyano-4-iodopyrid-2-yl)hydrazinedicarboxylate, MS spectrum (ES+): m/z=461 [MH+].

Tri-tert-butyl N,N',N'-(3-cyano-4-iodopyrid-2-yl)hydrazinetricarboxylate

To a mixture of 925 mg of 2-hydrazino-4-iodonicotinonitrile, 109 mg of N,N-dimethyaminopyridine and 2.6 mL of triethylamine in 45 mL of dichloromethane at 4° C. are added 3.9 g of di-tert-butyl dicarbonate (Boc₂O) in 20 mL of dichloromethane. The reaction is stirred for 30 minutes at 4° C. and the temperature is then allowed to rise to 20° C. Water is added and the mixture is extracted with ethyl acetate and then dried over magnesium sulfate and concentrated under reduced pressure. The oily brown residue is purified on silica Si60 (40-63 μm) (98/2 dichloromethane/methanol) to give 1.2 g of a yellow powder of tri-tert-butyl N,N',N'-(3-cyano-4-iodopyrid-2-yl)hydrazinetricarboxylate.

m.p.=138° C. (Köfler).
MS spectrum (ES+): m/z=561 [MH+]
Suzuki Coupling (X=C) with a di-Boc Derivative To a solution of 110 mg of di-tert-butyl (3-cyano-4-iodopyrid-2-yl)-hydrazinedicarboxylate and 122 mg of 1-(2-fluoro-5-trifluoromethylphenyl)-3-[4-(4,4,5,5-tetramethyl-1,3,2-dioxaborolan-2-yl)phenyl]urea in 5.5 mL of dioxane are added 57 mg of NaHCO₃ in 1.7 mL of water. 26 mg of tetrakis(triphenylphosphine)palladium are then added and the reaction is refluxed at 100° C. After 2 hours 30 minutes, the pale yellow solution is cooled to 20° C. and 10 mL of ethyl acetate are added. The organic phase is washed twice with 8 mL of water and then with 8 mL of brine. After drying over magnesium sulfate and concentrating under reduced pressure, the residual yellow oil is purified on a prepacked Biotage KP-Sil column of 60 Å SiO$_2$ 32-63 μm (9/1 cyclohexane/ethyl acetate). 114 mg of di-tert-butyl (3-cyano-4-{4-[3-(2-fluoro-5-trifluoromethylphenyl)ureido]phenyl}pyrid-2-yl)hydrazinedicarboxylate are obtained.

MS spectrum (ES+): m/z=631 [MH+]

Suzuki Coupling (X=C) with a Tri-Boc Derivative

To a solution of 108 mg of tri-tert-butyl N,N',N'-(3-cyano-4-iodopyrid-2-yl)-hydrazinetricarboxylate and 98 mg of 1-(2-fluoro-5-trifluoromethylphenyl)-3-[4-(4,4,5,5-tetramethyl-1,3,2-dioxaborolan-2-yl)phenyl]urea in 4.5 mL of dioxane are added 45.4 mg of NaHCO$_3$ in 1.4 mL of water. 20.3 mg of tetrakis(triphenylphosphine)palladium are then added and the reaction is refluxed at 100° C. After 2 hours 30 minutes, the pale yellow solution is cooled to 20° C. and 10 mL of ethyl acetate are added. The organic phase is washed twice with 8 mL of water and then with 8 mL of brine. After drying over magnesium sulfate and concentrating under reduced pressure, the residual yellow oil is purified on a prepacked Biotage KP-Sil column of 60 Å SiO$_2$ 32-63 μm (9/1 and then 7/3 cyclohexane/ethyl acetate). A fraction of 86 mg of tri-tert-butyl N,N',N'-(3-cyano-4-{4-[3-(2-fluoro-5-trifluoromethylphenyl)ureido]phenyl}pyrid-2-yl)hydrazinetricarboxylate and a fraction of 31 mg of di-tert-butyl (3-cyano-4-{4-[3-(2-fluoro-5-trifluoromethylphenyl)ureido]phenyl}pyrid-2-yl)hydrazinedicarboxylate are obtained.

MS spectrum (ES+): m/z=731 [MH+]

1-[4-(3-Amino-1H-pyrazolo[3,4-b]pyrid-4-yl)phenyl]-3-(2-fluoro-5-trifluoromethyl-phenyl)urea (from the di-Boc derivative)

To a solution of 111 mg of di-tert-butyl (3-cyano-4-{4-[3-(2-fluoro-5-trifluoromethylphenyl)ureido]phenyl}pyrid-2-yl)hydrazinedicarboxylate in 4 mL of dichloromethane at 20° C. is added 0.3 mL of trifluoroacetic acid containing 10% anisole, and the reaction is stirred for 4 hours. The reaction medium is concentrated under reduced pressure to give an orange-red solid. This residue is purified on a prepacked Biotage KP-Sil column of 60 Å SiO$_2$ 32-63 μm (gradient: 95/5 to 90/10 dichloromethane/solution A; solution A=38/17/2 dichloromethane/methanol/aqueous ammonia). 56 mg of a beige-coloured powder of 1-[4-(3-amino-1H-pyrazolo[3,4-b]pyrid-4-yl)phenyl]-3-(2-fluoro-5-trifluoromethylphenyl)urea are obtained, the characteristics of which are as follows:

IR spectrum (KBr): 3370; 3300; 1717; 1604; 1541; 1443; 1317; 1310; 1205; 1184; 1122; 1114; 1069 and 818 cm$^{-1}$ $^1$H NMR spectrum (300 MHz, (CD$_3$)$_2$SO-d6, δ in ppm): 4.58 (broad s, 2H); 6.91 (d, J=5.0 Hz, 1H); 7.41 (dm, J=9.0 Hz, 1H); 7.52 (broad t, J=9.0 Hz, 1H); 7.56 (broad d, J=8.5 Hz, 2H); 7.68 (broad d, J=8.5 Hz, 2H); 8.37 (d, J=5.0 Hz, 1H); 8.62 (broad dd, J=2.5 and 7.5 Hz, 1H); 9.13 (broad m, 1H); 9.57 (broad m, 1H); 12.25 (broad s, 1H)

m.p.=175° C. dec. (Köfler).

In a similar manner, 1-[4-(3-amino-1H-pyrazolo[3,4-b]pyrid-4-yl)phenyl]-3-(2-fluoro-5-trifluoromethylphenyl)urea may be obtained from a tri-Boc derivative as follows:

To a solution of 81 mg of the derivative tri-tert-butyl N,N',N'-(3-cyano-4-{4-[3-(2-fluoro-5-trifluoromethylphenyl)ureido]phenyl}pyrid-2-yl)hydrazinetricarboxylate in 3 mL of dichloromethane at 20° C. is added 0.2 mL of trifluoroacetic acid containing 10% anisole, and the reaction is stirred overnight. The reaction medium is concentrated under reduced pressure to give an orange-red solid. This residue is purified on a prepacked Biotage KP-Sil column of 60 Å SiO$_2$ 32-63 μm (gradient: 95/5 and then 90/10 dichloromethane/solution A; solution A=38/17/2 dichloromethane/methanol/aqueous ammonia). 27 mg of a beige-coloured powder of 1-[4-(3-amino-1H-pyrazolo[3,4-b]pyrid-4-yl)phenyl]-3-(2-fluoro-5-trifluoromethylphenyl)urea are obtained.

EXAMPLE 2

1-[5-(3-Amino-1H-pyrazolo[3,4-b]pyrid-4-yl)pyrid-2-yl]-3-(2-fluoro-5-trifluoromethylphenyl)urea

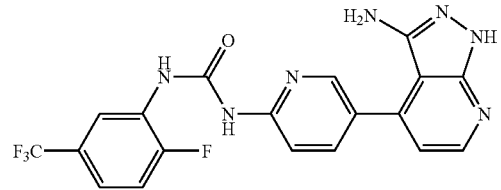

Suzuki Coupling (X=N)

To a solution of 150 mg of tri-tert-butyl N,N',N'-(3-cyano-4-iodopyrid-2-yl)-hydrazinetricarboxylate and 136 mg of 1-(2-fluoro-5-trifluoromethylphenyl)-3-[5-(4,4,5,5-tetramethyl-1,3,2-dioxaborolan-2-yl)pyrid-2-yl]urea in 6.2 mL of dioxane are added 63 mg of NaHCO$_3$ in 1.9 mL of water. 29 mg of tetrakis(triphenylphosphine)palladium are then added and the reaction is refluxed at 100° C. After 2 hours 30 minutes, the yellow solution is cooled to 20° C. and 10 mL of ethyl acetate are added. The organic phase is washed twice with 8 mL of water and then with 8 mL of brine. After drying over magnesium sulfate and concentrating under reduced pressure the residual yellow oil is purified on a prepacked Biotage KP-Sil column of 60 Å SiO$_2$ 32-63 μm (gradient: 98/2 to 95/5 dichloromethane/solution A; solution A=38/17/2 dichloromethane/methanol/aqueous ammonia). 67 mg of tri-tert-butyl N,N',N'-{3'-cyano-6-[3-(2-fluoro-5-trifluoromethyl phenyl)ureido][3,4']bipyridyl-2'-yl}-hydrazinetricarboxylate (MS spectrum (ES+): m/z=732 [MH+]) and 55 mg of di-tert-butyl {3'-cyano-6-[3-(2-fluoro-5-trifluoromethyl phenyl)ureido][3,4']bipyridyl-2'-yl}hydrazinedicarboxylate (MS spectrum (ES+): m/z=632 [MH+]) are obtained.

1-[5-(3-Amino-1H-pyrazolo[3,4-b]pyrid-4-yl)pyrid-2-yl]-3-(2-fluoro-5-trifluoromethylphenyl)urea To a solution of 55 mg of di-tert-butyl {3'-cyano-6-[3-(2-fluoro-5-trifluoro-methylphenyl)ureido][3,4']bipyridyl-2'-yl}hydrazinedicarboxylate in 2 mL of dichloromethane at 20° C. is added 0.15 mL of trifluoroacetic acid containing 10% anisole, and the reaction is stirred for 2 hours.

Separately, to a solution of 67 mg of the derivative tri-tert-butyl N,N',N'-{3'-cyano-6-[3-(2-fluoro-5-trifluoromethylphenyl)ureido][3,4']bipyridyl-2'-yl}hydrazinetricarboxylate in 3 mL of dichloromethane at 20° C. is added 0.16 mL of trifluoroacetic acid containing 10% anisole, and the reaction is stirred for 2 hours.

The brown-red reaction media are combined and concentrated under reduced pressure to give an orange-red solid. This residue is purified on a prepacked Biotage KP-Sil column of 60 Å SiO$_2$ 32-63 μm (gradient: 95/5 to 90/10 and then 70/30 dichloromethane/solution A; solution A=38/17/2 dichloro-methane/methanol/aqueous ammonia). A product is obtained, which is taken up in ethyl acetate and washed with water to remove the ammonium trifluoroacetate. After drying over magnesium sulfate and concentrating under reduced pressure, 58 mg of a beige-yellow powder of 1-[5-(3-amino-1H-pyrazolo[3,4-b]pyrid-4-yl)pyrid-2-yl]-3-(2-fluoro-5-trifluoromethylphenyl)urea are obtained, the characteristics of which are as follows:

IR spectrum (KBr): 3209; 1708; 1610; 1571; 1441; 1376; 1302; 1250; 1168; 1119; 1071; 822 and 616 cm$^{-1}$ $^1$H NMR spectrum (300 MHz, (CD$_3$)$_2$SO-d6, δ in ppm): 4.70 (broad s, 2H); 7.00 (d, J=5.0 Hz, 1H); 7.45 (dm, J=9.0 Hz, 1H); 7.55 (broad t, J=9.0 Hz, 1H); 7.65 (broad d, J=8.5 Hz, 1H); 8.06 (dd, J=2.5 and 8.5 Hz, 1H); 8.41 (d, J=5.0 Hz, 1H); 8.54 (d, J=2.5 Hz, 1H); 8.67 (dd, J=2.5 and 7.5 Hz, 1H); 10.15 (broad s, 1H); 11.15 (very broad m, 1H); 12.35 (broad m, 1H)

m.p.=>260° C. (Köfler).

EXAMPLE 3

1-[4-(3-Amino-1H-pyrazolo[4,3-c]pyrid-4-yl)phenyl]-3-(2-fluoro-5-trifluoromethylphenyl)urea

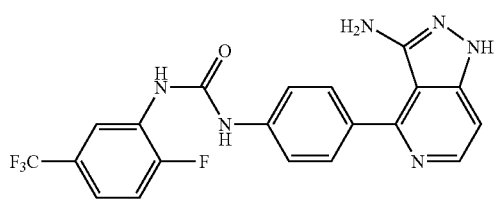

3-Amino-1H-pyrazolo[4,3-c]pyrid-4-ol

A mixture of 1.2 g of 2-hydroxy-4-methoxynicotinonitrile and 30 mL of hydrazine hydrate is maintained at 140° C. for 18 hours in a bomb. The reaction medium is then evaporated to dryness. The residue is taken up in ethyl ether, and the resulting suspension is filtered. 1.1 g of 3-amino-1H-pyrazolo[4,3-c]pyrid-4-ol are obtained in the form of a grey solid.

MS: 150$^+$=M$^{+\circ}$; m.p.=240° C. dec. (Köfler).

4-Bromo-1H-pyrazolo[4,3-c]pyrid-3-ylamine

To 3.5 g of POBr$_3$ melted at 45° C. is added 0.4 g of 3-amino-1H-pyrazolo[4,3-c]pyrid-4-ol, and the suspension is then maintained at 70° C. for 4 hours. The resulting mixture is allowed to cool and is hydrolysed, cautiously, with sodium bicarbonate solution. The mixture is extracted with ethyl acetate. The organic phase is isolated and dried over magnesium sulfate, filtered and then concentrated under reduced pressure. 0.33 g of 4-bromo-1H-pyrazolo[4,3-c]pyrid-3-ylamine is obtained in the form of a cream-coloured solid.

MS: 212$^+$=M$^{+\circ}$; m.p.=230° C. dec. (Köfler).

1-[4-(3-Amino-1H-pyrazolo[4,3-c]pyrid-4-yl)phenyl]-3-(2-fluoro-5-trifluoromethylphenyl)urea To a solution of 53 mg of 4-bromo-1H-pyrazolo[4,3-c]pyrid-3-ylamine in 6 mL of dioxane are added 127 mg of 1-(2-fluoro-5-trifluoromethylphenyl)-3-[4-(4,4,5,5-tetramethyl-1,3,2-dioxaborolan-2-yl)phenyl]urea, 60 mg of sodium bicarbonate in 1.8 mL of water and 30 mg of tetrakis(triphenylphosphine)palladium. The reaction is heated in a bath at 100° C. for 2 hours. The mixture is allowed to cool and ethyl acetate is then added. The mixture is washed with water. The organic phase is dried over magnesium sulfate and then concentrated under reduced pressure. The oily residue is purified on a prepacked Biotage KP-Sil column of 60 Å SiO$_2$ 32-63 μm (gradient: 90/10 to 70/30 dichloromethane/solution A; solution A=38/17/2 dichloromethane/methanol/aqueous ammonia). 34 mg of 1-[4-(3-amino-1H-pyrazolo[4,3-c]pyrid-4-yl)phenyl]-3-(2-fluoro-5-trifluoromethylphenyl)urea are obtained in the form of a cream-coloured solid, the characteristics of which are as follows:

MS: 431$^+$=MH$^+$

IR spectrum (KBr): 3354; 1717; 1605; 1542; 1442; 1339; 1313; 1181; 1119; 816 and 615 cm$^{-1}$ $^1$H NMR spectrum (300 MHz, (CD$_3$)$_2$SO-d6, δ in ppm): 4.72 (broad s, 2H); 7.20 (d, J=5.5 Hz, 1H); 7.41 (broad m, 1H); 7.51 (broad t, J=9.5 Hz, 1H); from 7.59 to 7.72 (m, 4H); 8.22 (d, J=5.5 Hz, 1H); 8.65 (broad d, J=7.5 Hz, 1H); 8.96 (broad s, 1H); 9.37 (s, 1H); 12.1 (broad s, 1H).

EXAMPLE 4

1-[5-(3-Amino-1H-pyrazolo[4,3-c]pyrid-4-yl)pyrid-2-yl]-3-(2-fluoro-5-trifluoromethylphenyl)urea

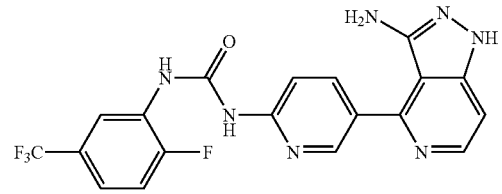

1-[5-(3-Amino-1H-pyrazolo[4,3-c]pyrid-4-yl)pyrid-2-yl]-3-(2-fluoro-5-trifluoromethylphenyl)urea To a solution of 106 mg of 4-bromo-1H-pyrazolo[4,3-c]pyrid-3-ylamine in 10 mL of dioxane are added 252 mg of 1-(2-fluoro-5-trifluoromethylphenyl)-3-[5-(4,4,5,5-tetramethyl-1,3,2-dioxaborolan-2-yl)pyrid-2-yl]urea, 120 mg of sodium bicarbonate in 3 mL of water, and 60 mg of tetrakis(triphenylphosphine)palladium. The reaction is heated in a bath at 100° C. for 2 hours. The mixture is allowed to cool, ethyl acetate is then added and the mixture is washed with water. The organic phase is dried over magnesium sulfate and then concentrated under reduced pressure. The oily residue is purified on a prepacked Biotage KP-Sil column of 60 Å SiO$_2$ 32-63 μm (gradient: 90/10 to 70/30 dichloromethane/solution A; solution A=38/17/2 dichloromethane/methanol/aqueous ammonia). 35 mg of a yellow solid of 1-[5-(3-amino-1H-pyrazolo[4,3-c]pyrid-4-yl)pyrid-2-yl]-3-(2-fluoro-5-trifluoromethylphenyl)urea are obtained, the characteristics of which are as follows:

MS: 432$^+$=MH$^+$

IR spectrum (KBr): 3404; 3224; 1693; 1609; 1572; 1441; 1340; 1300; 1246; 1119; 819 and 615 cm$^{-1}$ $^1$H NMR spectrum (300 MHz, (CD$_3$)$_2$SO-d6, δ in ppm): 4.88 (broad s, 2H); 7.25 (d, J=6.0 Hz, 1H); 7.44 (broad m, 1H); from 7.50 to 7.53 (m, 2H); 8.15 (dd, J=2.5 and 8.5 Hz, 1H); 8.26 (d, J=6.0 Hz, 1H); 8.63 (d, J=2.5 Hz, 1H); 8.70 (broad d, J=7.5 Hz, 1H); 10.15 (broad s, 1H); 11.3 (very broad m, 1H); 12.2 (broad s, 1H).

EXAMPLE 5

1-[4-(3-Amino-1H-pyrazolo[3,4-b]pyrid-4-yl)phenyl]-3-(2-methoxy-5-trifluoromethylphenyl)urea

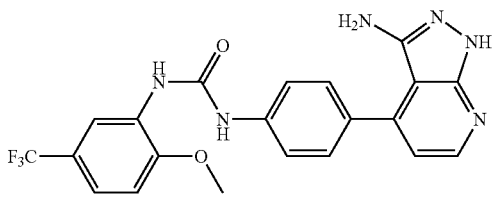

1-(2-Methoxy-4-trifluoromethylphenyl)-3-[4-(4,4,5,5-tetramethyl-1,3,2-dioxaborolan-2-yl)phenyl]urea To a solution of 1 g of 2-methoxy-4-(trifluoromethyl) aniline and 128 mg of 4-dimethylaminopyridine in 150 mL of tetrahydrofuran and 1.5 mL of triethylamine are added, at 20° C., 1.28 g of 2-(4-isocyanatophenyl)-4,4,5,5-tetramethyl-1,3,2-dioxaborolane. After 4 hours, the reaction is evaporated to dryness under reduced pressure. The residue is taken up in a mixture of ethyl acetate and water. The organic phase is dried over magnesium sulfate and then concentrated under reduced pressure. The residual yellow oil is purified on a prepacked Biotage KP-Sil column of 60 Å SiO$_2$ 32-63 μm (eluent: 8/2 cyclohexane/ethyl acetate). A pale yellow powder is obtained, which is taken up in methanol. An insoluble white material is formed, which is separated out by filtration, and the filtrate is then evaporated to dryness under reduced pressure to give 0.47 g of a pale yellow powder of 1-(2-methoxy-4-trifluoromethylphenyl)-3-[4-(4,4,5,5-tetramethyl-1,3,2-dioxaborolan-2-yl)phenyl]urea.

MS: 437$^+$=MH$^+$ $^1$H NMR spectrum (300 MHz, (CD$_3$)$_2$SO-d6, δ in ppm): 1.30 (s: 12H); 3.99 (s: 3H); 7.22 (d, J=9 Hz: 1H); 7.34 (dd, J=9 and 1 Hz: 1H); 7.50 (d, J=9: 2H); 7.63 (d, J=9 Hz: 2H); 8.56 (mt: 2H); 9.58 (s: 1H).

Di-Boc and tri-Boc derivatives of 1-[4-(3-cyano-2-hydrazinopyrid-4-yl)phenyl]-3-(2-methoxy-5-trifluoromethylphenyl)urea To a solution of 0.27 g of tri-tert-butyl N,N',N'-(3-cyano-4-iodopyrid-2-yl)-hydrazinetricarboxylate in 14 mL of dioxane, at 20° C., are added 273 mg of 1-(2-methoxy-4-trifluoromethylphenyl)-3-[4-(4,4,5,5-tetramethyl-1,3,2-dioxaborolan-2-yl)phenyl]urea. To this solution are added a solution of 114 mg of sodium bicarbonate in 4 mL of water, and then 51 mg of tetrakis(triphenylphosphine)palladium. The reaction is refluxed at 10° C. for 2 hours 30 minutes. The pale yellow solution is cooled, and ethyl acetate is then added. The mixture is washed with water and then with brine. The organic phase is dried over magnesium sulfate and then concentrated under reduced pressure. The orange-yellow resin obtained is purified on a prepacked Biotage KP-Sil column of 60 Å SiO$_2$ 32-63 μm (eluent: 7/3 cyclohexane/ethyl acetate, then 9/1 dichloromethane/solution A; solution A=38/17/2 dichloromethane/methanol/aqueous ammonia). 0.33 g of a yellow powder of a mixture of di-Boc and tri-Boc derivatives of 1-[4-(3-cyano-2-hydrazinopyrid-4-yl)phenyl]-3-(2-methoxy-5-trifluoromethylphenyl)urea is obtained.

1-[4-(3-Amino-1H-pyrazolo[3,4-b]pyrid-4-yl)phenyl]-3-(2-methoxy-5-trifluoromethylphenyl)urea To a solution of 272 mg of a mixture of di-Boc and tri-Boc derivatives of 1-[4-(3-cyano-2-hydrazinopyrid-4-yl)phenyl]-3-(2-methoxy-5-trifluoromethylphenyl)urea in 7.7 mL of dichloromethane at 20° C. is added 0.62 mL of trifluoroacetic acid containing 10% of anisole. After stirring for 3 hours, the orange-red medium is concentrated to dryness under reduced pressure. The residual orange-red oil is purified on a prepacked Biotage KP-Sil column of 60 Å SiO$_2$ 32-63 μm (gradient: 90/10 to 70/30 dichloromethane/solution A; solution A=38/17/2 dichloromethane/methanol/aqueous ammonia). A beige-yellow powder is obtained, which is taken up in ethyl acetate. The solution is washed with water. The organic phase is dried over magnesium sulfate and then concentrated under reduced pressure to give 61 mg of a yellow powder of 1-[4-(3-amino-1H-pyrazolo[3,4-b]pyrid-4-yl)phenyl]-3-(2-methoxy-5-trifluoromethylphenyl)urea, the characteristics of which are as follows:

MS: 443$^+$=MH$^+$

IR spectrum (KBr): 3380; 1706; 1675; 1600; 1539; 1314; 1269; 1134; 1117; 822 and 622 cm$^{-1}$ $^1$H NMR spectrum (400 MHz, (CD$_3$)$_2$SO-d6, δ in ppm): 3.99 (s, 3H); 4.59 (broad s, 2H); 6.91 (d, J=5.0 Hz, 1H); 7.22 (d, J=8.5 Hz, 1H); 7.34 (broad dd, J=2.0 and 8.5 Hz, 1H); 7.55 (broad d, J=8.5 Hz, 2H); 7.66 (broad d, J=8.5 Hz, 2H); 8.37 (d, J=5.0 Hz, 1H); from 8.56 to 8.61 (m, 2H); 9.66 (s, 1H); 12.25 (broad s, 1H).

m.p.=>260° C. (Köfler).

EXAMPLE 6

1-[5-(3-Amino-1H-pyrazolo[3,4-b]pyrid-4-yl)pyrid-2-yl]-3-(2-methoxy-5-trifluoromethylphenyl)urea

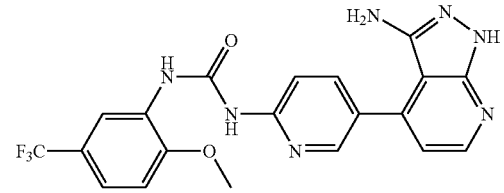

1-(5-Bromopyrid-2-yl)-3-(2-methoxy-5-trifluoromethylphenyl)urea 3.32 g of 2-methoxy-5-trifluoromethylphenylamine in 30 mL of tetrahydrofuran are added dropwise to a solution of 1.8 g of triphosgene in 180 mL of tetrahydrofuran at 0° C. 4.95 mL of triethylamine are then added and the reaction is stirred at this temperature for 10 minutes. The temperature is allowed to rise to 20° C. and the mixture is stirred for 1 hour 15 minutes. A solution of 3 g of 2-amino-5-bromopyridine in 30 mL of THF is then added dropwise. After 16 hours, the suspension is filtered and the filtrate is then concentrated under reduced pressure. The residue is taken up in a mixture of ethyl acetate and water. An insoluble white precipitate is obtained, which is filtered off, washed with ethyl acetate and then dried under vacuum. 3.3 g of a white powder of 1-(5-bromopyrid-2-yl)-3-(2-methoxy-5-trifluoromethylphenyl)urea are obtained.

MS: 390⁺=MH⁺

1-(2-Methoxy-5-trifluoromethylphenyl)-3-[5-(4,4,5,5-tetramethyl-1,3,2-dioxaborolan-2-yl)pyrid-2-yl]urea To a solution of 51 mg of tricyclohexylphosphine in 12 mL of dioxane at 20° C. are added 30 mg of bis(dibenzylideneacetone)palladium. The violet-brown solution is stirred for 30 minutes, and 500 mg of 1-(5-bromopyrid-2-yl)-3-(2-methoxy-5-trifluoromethylphenyl)urea and 190 mg of potassium acetate are then added. The suspension is refluxed for 3 hours 15 minutes and the violet-red solution is then cooled to 20° C. and concentrated to dryness under reduced pressure. A green-grey residue is obtained, which is washed in a mixture of ethyl acetate and water. The organic phase is filtered and the yellow filtrate is concentrated under reduced pressure. The solid residue obtained is taken up in methanol. A precipitate forms, which is filtered off and washed with methanol and ethyl acetate. 244 mg of a pale yellow powder of 1-(2-methoxy-5-trifluoromethylphenyl)-3-[5-(4,4,5,5-tetramethyl-1,3,2-dioxaborolan-2-yl)pyrid-2-yl]urea are obtained.

MS: 437⁺=M⁺°

¹H NMR spectrum (300 MHz, (CD₃)₂SO-d6, δ in ppm): 1.32 (s: 12H); 4.03 (s: 3H); 7.25 (d, J=9.5 Hz: 1H); 7.34 (broad d, J=9 Hz: 1H); 7.39 (dd, J=9.5 and 1 Hz: 1H); 7.96 (dd, J=9 and 2 Hz: 1H); 8.52 (d, J=1 Hz: 1H); 8.63 (d, J=2 Hz: 1H); 10.20 (s: 1H); 11.50 (broad s: 1H).

Di-Boc and tri-Boc derivatives of 1-(3'-cyano-2'-hydrazino[3,4']bipyridyl-6-yl)-3-(2-methoxy-5-trifluoromethylphenyl)urea 234 mg of 1-(2-methoxy-5-trifluoromethylphenyl)-3-[5-(4,4,5,5-tetramethyl-1,3,2-dioxaborolan-2-yl)pyrid-2-yl]urea are added at 20° C. to a solution of 0.3 g of tri-tert-butyl N,N',N'-(3-cyano-4-iodopyrid-2-yl)hydrazinetricarboxylate in 16.5 mL of dioxane. A solution of 126 mg of sodium bicarbonate in 4.5 mL of water is then added, followed by addition of 57 mg of tetrakis(triphenylphosphine)palladium. The yellow suspension obtained is refluxed at 100° C. for 2 hours 30 minutes. After cooling, ethyl acetate is added. The organic phase is washed with water and then with brine. The organic phase is dried over magnesium sulfate and then concentrated to dryness under reduced pressure. The residual orange-yellow resin is purified on a prepacked Biotage KP-Sil column of 60 Å SiO₂ 32-63 μm (eluent: 7/3 cyclohexane/ethyl acetate, and then 95/5 dichloromethane/solution A; solution A=38/17/2 dichloromethane/methanol/aqueous ammonia). 265 mg of a mixture of di-Boc and tri-Boc derivatives of 1-(3'-cyano-2'-hydrazino-[3,4']bipyridyl-6-yl)-3-(2-methoxy-5-trifluoromethylphenyl)urea are obtained in the form of a yellow powder.

1-[5-(3-Amino-1H-pyrazolo[3,4-b]pyrid-4-yl)pyrid-2-yl]-3-(2-methoxy-5-trifluoromethylphenyl)urea 0.8 mL of trifluoroacetic acid containing 10% of anisole is added at 20° C. to a solution of 242 mg of a mixture of di-Boc and tri-Boc derivatives of 1-(3'-cyano-2'-hydrazino[3,4']bipyridyl-6-yl)-3-(2-methoxy-5-trifluoromethylphenyl)urea in 7 mL of dichloromethane. After stirring for 2 hours 30 minutes, the orange-red reaction medium is concentrated to dryness under reduced pressure. The residual orange-red oil is purified on a prepacked Biotage KP-Sil column of 60 Å SiO₂ 32-63 μm (gradient: 90/10 to 70/30 dichloromethane/solution A; solution A=38/17/2 dichloromethane/methanol/aqueous ammonia). 130 mg of a beige-yellow powder of 1-[5-(3-amino-1H-pyrazolo[3,4-b]pyrid-4-yl)pyrid-2-yl]-3-(2-methoxy-5-trifluoromethylphenyl)urea are obtained, the characteristics of which are as follows:

MS: 444⁺=MH⁺

IR spectrum (KBr): 3420; 3219; 1684; 1613; 1586; 1438; 1303; 1271; 1247; 1136; 834 and 622 cm⁻¹

¹H NMR spectrum (300 MHz, (CD₃)₂SO-d6, δ in ppm): 4.02 (s, 3H); 4.72 (very broad m, 2H); 7.01 (d, J=5.0 Hz, 1H); 7.24 (d, J=8.5 Hz, 1H); 7.37 (broad dd, J=2.0 and 8.5 Hz, 1H); 7.48 (broad d, J=8.5 Hz, 1H); 8.03 (dd, J=2.5 and 8.5 Hz, 1H); 8.41 (d, J=5.0 Hz, 1H); 8.59 (d, J=2.5 Hz, 1H); 8.64 (d, J=2.0 Hz, 1H); 10.2 (s, 1H); 11.5 (very broad m, 1H); 12.35 (broad s, 1H).

m.p.=>260° C. (Köfler).

EXAMPLE 7

1-[4-(3-Amino-1H-pyrazolo[3,4-b]pyrid-4-yl)phenyl]-3-(2-fluoro-5-trifluoromethylphenyl)urea

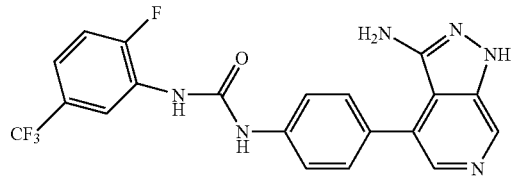

1-[4-(5-chloro-4-cyanopyrid-3-yl)phenyl]-3-(2-fluoro-5-trifluoromethylphenyl)urea To a solution of 346 mg of 3,5-dichloroisonicotinonitrile and 959 mg of 1-(2-fluoro-5-trifluoromethylphenyl)-3-[4-(4,4,5,5-tetramethyl-1,3,2-dioxaborolan-2-yl)phenyl]urea in 24 mL of dioxane are added 462 mg of NaHCO₃ in 14.4 mL of water. 462 mg of tetrakis(triphenylphosphine)palladium are then added and the reaction is refluxed for 5 hours and then left overnight at 20° C. 20 mL of water are then added and the mixture is extracted with 2×60 mL of ethyl acetate. The organic phase is dried over magnesium sulfate and then concentrated under reduced pressure. The brown oil is purified on a prepacked Merck cartridge of 30 g of SiO₂ 15-40 μm (dichloromethane and then 99/1 dichloromethane/methanol). 290 mg of yellow crystals of 1-[4-(5-chloro-4-cyanopyrid-3-yl)phenyl]-3-(2-fluoro-5-trifluoromethylphenyl)urea are obtained.

MS spectrum (ES⁺): m/z=435 [MH⁺]

¹H NMR spectrum at 400 MHz on a Brüker Avance DRX-400 machine chemical shifts (δ in ppm)—solvent: (DMSO-d6) referenced at 2.50 ppm at a temperature of 303K:

7.41 (m, 1H); 7.51 (dd, J=8.5 and 10.5 Hz, 1H); 7.68 (broad s, 4H); 8.62 (dd, J=2.0 and 7.0 Hz, 1H); 8.85 (s, 1H); 8.94 (s, 1H); 9.04 (broad m, 1H); 9.49 (broad m, 1H).

1-[4-(3-Amino-1H-pyrazolo[3,4-c]pyrid-4-yl)phenyl]-3-(2-fluoro-5-trifluoromethylphenyl)urea To a solution of 145 mg of 1-[4-(5-chloro-4-cyanopyrid-3-yl)phenyl]-3-(2-fluoro-5-trifluoromethylphenyl)urea in 2 mL of EtOH at 20° C. is added 0.05 mL of hydrazine hydrate.

The reaction is refluxed for 5 hours 30 minutes. The reaction is incomplete, and a further 1 mL of EtOH and 0.05 mL of hydrazine hydrate are added, and refluxing is continued for a further 18 hours 30 minutes. The mixture is allowed to cool to 20° C. and is concentrated under a stream of nitrogen. The residue is purified by chromatography on silica gel: prepacked Merck cartridge of 30 g of SiO₂ 15-40 μm (dichloromethane; then 95/5 dichloromethane/methanol; then 1/1 dichloromethane/methanol; then 82/15/3 dichloromethane/methanol/NH₄OH). An impure beige-coloured oil is recovered, which is chromatographed again under the same conditions. The product is still impure, and is purified by basic preparative HPLC: conditions: column: Nucleodur Gravity C18 5 μm (N° cat Macherey Nagel: 762101; series 4055902; batch 3044); flow rate: 20 mL/minute; detection 254 nm (UV118, Gilson); gradient from 10 to 95% of acetonitrile in water containing 10 mM ammonium formate according to the following protocol: (t (min.): acetonitrile (%)): 0: 10; 2: 10; 25: 95; 33: 95; 34: 10. 19 mg of a yellow powder of 1-[4-(3-amino-1H-pyrazolo[3,4-c]pyrid-4-yl)phenyl]-3-(2-fluoro-5-trifluoromethylphenyl)urea are obtained.

m.p.=196° C. (Köfler)

MS spectrum (ES⁺): m/z=431 [MH⁺]

¹H NMR spectrum at 400 MHz on a Brüker Avance DRX-400 machine, chemical shifts (δ in ppm)—solvent (DMSO-d6) referenced at 2.50 ppm at 303 K: 4.61 (s, 2H); 7.40 (m, 1H); 7.50 (m, 3H); 7.66 (broad d, J=8.5 Hz, 2H); 7.94 (s, 1H); 8.63 (dd, J=2.0 and 7.0 Hz, 1H); 8.74 (s, 1H); 9.10 (broad m, 1H); 9.51 (s, 1H); 12.3 (broad m, 1H).

IR: (KBr): 1610; 1531; 1443; 1340; 1314; 1265; 1195; 1166; 1118; 1069; 820 and 615 cm⁻¹

EXAMPLE 8

1-[4-(3-Amino-1H-pyrazolo[4,3-c]pyrid-4-yl)phenyl]-3-phenylurea

Prepared According to Scheme 2

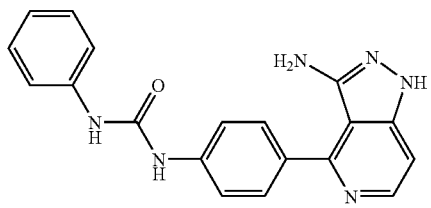

1-Phenyl-3-[4-(4,4,5,5-tetramethyl-1,3,2-dioxaborolan-2-yl)phenyl]urea

To a solution of 490 mg of 2-(4-isocyanatophenyl)-4,4,5,5-tetramethyl-1,3,2-dioxaborolane and 203 mg of triethylamine in 5 ml of tetrahydrofuran are added 198 mg of aniline. The solution is stirred for 12 hours at 20° C. under argon. 10 ml of methanol are added to the reaction mixture. The mixture is then stirred at 20° C. for 15 minutes. After concentrating the mixture under reduced pressure, 630 mg of 1-phenyl-3-[4-(4,4,5,5-tetramethyl-1,3,2-dioxaborolan-2-yl)phenyl]urea are obtained, the characteristics of which are as follows:

MS: 339 (+)=(M+H) (+)

337 (−)=(M−H) (−)

IR spectrum (KBr): 3332; 2976; 1656; 1593; 1543; 1400; 1361; 1143; 1092; 963; 860 and 655 cm⁻¹

¹H NMR spectrum (400 MHz, (CD₃)₂SO, δ in ppm): 1.29 (s.12H); 6.98 (broad t, J=7.5 Hz, 1H); 7.28 (broad t, J=8.0 Hz, 2H); from 7.41 to 7.49 (m, 4H); 7.59 (broad d, j=8.0 Hz, 2H); 8.70 (s, 1H); 8.82 (s.1H).

1-[4-(3-Amino-1H-pyrazolo[4,3-c]pyrid-4-yl)phenyl]-3-phenylurea

To a solution of 65 mg of 4-bromo-1H-pyrazolo[4,3-c]pyrid-3-ylamine, prepared as described in Example 3, in 3 ml of dioxane are added 155 mg of 1-phenyl-3-[4-(4,4,5,5-tetramethyl-1,3,2-dioxaborolan-2-yl)phenyl]urea, 72 mg of sodium hydrogen carbonate in 1 ml of water and 53 mg of tetrakis(triphenylphosphine)palladium. The suspension is heated at 100° C. under argon for 2 hours. After cooling, the reaction mixture is poured into 50 ml of water and extracted three times with ethyl acetate. The combined organic phases are dried over magnesium sulfate and concentrated under reduced pressure to give 302 mg of crude product, which are purified on a prepacked Biotage KP-Sil column of 60 Å SiO₂ 32-63 μm (5/95 to 30/70 gradient of solution A in dichloromethane; solution A=38/17/2 dichloromethane/methanol/aqueous ammonia). 23 mg of a yellow powder of 1-[4-(3-amino-1H-pyrazolo[4,3-c]pyrid-4-yl)phenyl]-3-phenylurea are obtained, the characteristics of which are as follows:

MS: 344 (+)=M (+) (MS-EI)

IR spectrum (KBr): 3388; 1672; 1601; 1528; 1498; 1442; 1313; 1233; 1180; 1045; 752 and 693 cm⁻¹

¹H NMR spectrum (400 MHz, (CD₃)₂SO, δ in ppm): 4.71 (broad s, 2H); 6.99 (t, J=7.5 Hz, 1H); 7.19 (d, J=5.0 Hz, 1H); 7.30 (t, J=7.5 Hz, 2H); 7.48 (d, J=7.5 Hz, 2H); 7.62 (m, 4H); 8.21 (d, J=5.0 Hz, 1H); 8.73 (s, 1H); 8.89 (s, 1H); 12.1 (broad s, 1H).

m.p.=188° C. (Köfler)

EXAMPLE 9

1-[5-(3-Amino-1H-pyrazolo[4,3-c]pyrid-4-yl)pyrid-2-yl]-3-(2-methoxy-5-trifluoromethylphenyl)urea

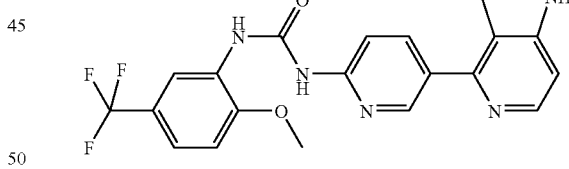

To a solution of 70 mg of 4-bromo-1H-pyrazolo[4,3-c]pyrid-3-ylamine in 3 ml of dioxane are added 215 mg of 1-(2-methoxy-5-trifluoromethylphenyl)-3-[5-(4,4,5,5-tetramethyl-1,3,2-dioxaborolan-2-yl)pyrid-2-yl]urea (prepared as described in Example 6), 77 mg of sodium hydrogen carbonate in 1 ml of water and 38 mg of tetrakis(triphenylphosphine)palladium. The suspension is heated at 80° C. under argon for 2 hours. After cooling, the reaction is poured into 50 ml of water and the mixture is extracted three times with a 90/10 ethyl acetate/methanol mixture. The combined organic phases are dried over magnesium sulfate and concentrated under reduced pressure. 393 mg of crude product are purified on a prepacked Biotage KP-Sil column of 60 Å SiO₂ 32-63 μm (5/95 to 30/70 gradient of solution A in dichloromethane; solution A=38/17/2 dichloromethane/methanol/aqueous ammonia). 16 mg of a yellow powder of 1-[5-(3-amino-1H- pyrazolo[4,3-c]pyrid-4-yl)pyrid-2-yl]-3-(2-methoxy-5-trif-luoromethylphenyl)urea are obtained, the characteristics of which are as follows:

LC-MS: 444 (+)=(M+H)(+)

IR spectrum (KBr): 3657; 3387; 3308; 3223; 2925; 1685; 1610; 1580; 1439; 1351; 1302; 1246; 1166; 1135; 1116; 1037; 807 and 542 cm$^{-1}$ $^1$H NMR spectrum (400 MHz, $(CD_3)_2SO$, δ in ppm): 4.02 (s, 3H); 4.89 (broad s, 2H); from 7.21 to 7.28 (m, 2H); 7.38 (d, J=8.5 Hz, 1H); 7.46 (broad d, J=8.5 Hz, 1H); 8.12 (dd, J=2.0 and 8.5 Hz, 1H); 8.27 (d, J=5.0 Hz, 1H); 8.63 (d, J=2.0 Hz, 1H); 8.69 (d, J=2.0 Hz, 1H); 10.15 (s, 1H); 11.65 (broad m, 1H); 12.2 (broad s, 1H).

m.p.=228° C. (Köfler)

EXAMPLE 10

1-[4-(3-Amino-1H-pyrazolo[4,3-c]pyrid-4-yl)phe-nyl]-3-(2-methoxy-5-trifluoromethylphenyl)urea

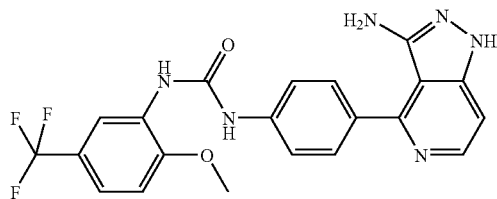

To a solution of 50 mg of 4-bromo-1H-pyrazolo[4,3-c]pyrid-3-ylamine in 3 ml of dioxane are added 122.8 mg of 1-(2-methoxy-5-trifluoromethylphenyl)-3-[4-(4,4,5,5-tet-ramethyl-1,3,2-dioxaborolan-2-yl)phenyl]urea, 99.5 mg of sodium carbonate in 1 ml of water and 54.24 mg of tetrakis (triphenylphosphine)-palladium. The suspension is heated at 80° C. under an argon atmosphere for 22 hours. After cooling, the reaction mixture is diluted with ethyl acetate and washed twice with water. The organic phase is dried over magnesium sulfate and concentrated under reduced pressure. 438 mg of crude product are purified on a prepacked Biotage KP-Sil column of 60 Å SiO$_2$ 32-63 µm (5/95 to 30/70 gradient of solution A in dichloromethane; solution A=38/17/2 dichlo-romethane/methanol/aqueous ammonia). 32 mg of a yellow powder of 1-[4-(3-amino-1H-pyrazolo[4,3-c]pyrid-4-yl)phe-nyl]-3-(2-methoxy-5-trifluoromethyl-phenyl)urea are obtained, the characteristics of which are as follows:

LC-MS: 443 (+)=(M+H) (+)

IR spectrum (KBr): 3326; 1691; 1605; 1542; 1447; 1314; 1270; 1217; 1120; 1024; 812 and 623 cm$^{-1}$ $^1$H NMR spectrum (400 MHz, $(CD_3)_2SO$, δ in ppm): 3.99 (s, 3H); 4.73 (broad s, 2H); 7.19 (d, J=5.0 Hz, 1H); 7.22 (d, J=8.5 Hz, 1H); 7.33 (broad d, J=8.5 Hz, 1H); 7.64 (m, 4H); 8.21 (d, J=5.0 Hz, 1H); 8.59 (m, 2H); 9.63 (s, 1H); 12.1 (broad s, 1H)

m.p.=200° C. (Köfler)

EXAMPLE 11

N-(2-{3-[4-(3-Amino-1H-pyrazolo[4,3-c]pyrid-4-yl) phenyl]ureido}-4-trifluoromethylphenyl)acetamide

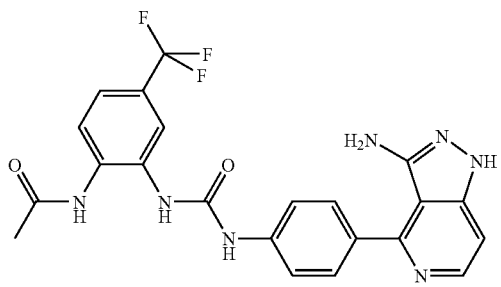

N-(2-{3-[4-(4,4,5,5-Tetramethyl-1,3,2-dioxaborolan-2-yl)phenyl]ureido}-4-trifluoromethylphenyl)aceta-mide Prepared According to Scheme 4

To a solution of 343 mg of N1-[2-amino-4-(trifluorom-ethyl)phenyl]acetamide and 39 mg of 4-dimethylaminopyri-dine in 50 mL of tetrahydrofuran and 0.45 mL of triethy-lamine are added, at 20° C., 385 mg of 2-(4-isocyanatophenyl)-4,4,5,5-tetramethyl-1,3,2-dioxaborolane. After reacting overnight at 40° C., the reaction is evaporated to dryness under reduced pressure. The residue is taken up in a mixture of dichloromethane and water. The organic phase is washed with 1N HCl, and the white precipitate is filtered by suction and washed with dichloromethane, and then dried under vacuum to give 356 mg of a white powder of N-(2-{3-[4-(4,4,5,5-tetramethyl-1,3,2-dioxaborolan-2-yl)phenyl]ure-ido}-4-trifluoromethylphenyl)acetamide, the characteristics of which are as follows:

MS-ES$^+$: 464(+)=(M+H)(+)
MS-ES$^-$: 462(−)=(M−H)(−)

$^1$H NMR spectrum (300 MHz, $(CD_3)_2SO$-d6, δ in ppm): 1.28 (s, 12H); 2.15 (broad s, 3H); 7.37 (broad d, J=8.5 Hz, 1H); 7.50 (d, J=8.5 Hz, 2H); 7.54 (partially masked d, J=8.5 Hz, 1H); 7.61 (d, J=8.5 Hz, 2H); 8.16 (broad s, 1H); 8.28 (broad s, 1H); 9.43 (broad s, 1H); 9.79 (broad s, 1H).

N-(2-{3-[4-(3-Amino-1H-pyrazolo[4,3-c]pyrid-4-yl) phenyl]ureido}-4-trifluoromethylphenyl)acetamide 4-Bromo-1H-pyrazolo[4,3-c]pyrid-3-ylamine and N-(2-{3-[4-(4,4,5,5-tetramethyl-1,3,2-dioxaborolan-2-yl)phenyl] ureido}-4-trifluoromethylphenyl)acetamide are coupled by Suzuki reaction according to a protocol similar to that for the preparation of Example 10. A yellow powder of N-(2-{3-[4-(3-amino-1H-pyrazolo[4,3-c]pyrid-4-yl)phenyl]ureido}-4-trifluoromethylphenyl)acetamide is obtained, the character-istics of which are as follows:

MS: 470 (+)=(M+H) (+)
468 (−)=(M−H) (−)
514 (−)=(M+formic acid-H) (−)

IR spectrum (KBr): 3390; 1667; 1605; 1528; 1436; 1336; 1315; 1247; 1167; 1126; 1042; 813 and 684 cm$^{-1}$ $^1$H NMR spectrum (400 MHz, $(CD_3)_2SO$, δ in ppm): 2.16 (s, 3H); 4.72 (s, 2H); 7.19 (d, J=5.0 Hz, 1H); 7.37 (broad d, J=8.5 Hz, 1H); 7.56 (d, J=8.5 Hz, 1H); 7.64 (m, 4H); 8.21 (d, J=5.0 Hz, 1H); 8.28 (m, 2H); 9.54 (broad s, 1H); 9.82 (broad s, 1H); 12.1 (broad s, 1H).

m.p.=182° C. (Köfler)

EXAMPLE 12

N-(2-{3-[4-(3-Amino-1H-pyrazolo[3,4-b]pyrid-4-yl)phenyl]ureido}-4-trifluoromethylphenyl)acetamide

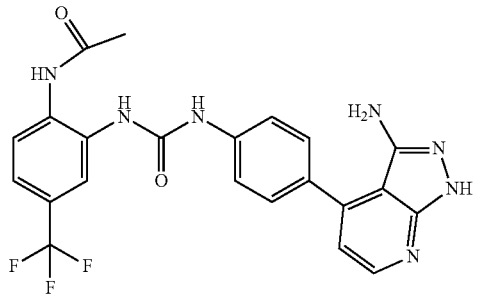

N,N',N'-tri-Boc derivative of N-(2-{3-[4-(3-cyano-2-hydrazinopyrid-4-yl)phenyl]-ureido}-4-trifluoromethylphenyl)acetamide Prepared According to Scheme 1

To a solution of 278 mg of tri-tert-butyl N,N',N'-(3-cyano-4-iodopyrid-2-yl)-hydrazinetricarboxylate (prepared according to Example 1) in 15 mL of dioxane, at 20° C., are added 282 mg of N-(2-{3-[4-(4,4,5,5-tetramethyl-1,3,2-dioxaborolan-2-yl)phenyl]ureido}-4-trifluoromethylphenyl)acetamide. To this solution is added a solution of 117 mg of sodium bicarbonate in 4.2 mL of water, followed by addition of 53 mg of tetrakis(triphenylphosphine)palladium. The reaction is refluxed at 100° C. for 2 hours 30 minutes. The pale yellow solution is cooled, and ethyl acetate is then added. The mixture is washed with water and then with brine. The organic phase is dried over magnesium sulfate and then concentrated under reduced pressure. The orange-yellow resin obtained is purified on a prepacked Biotage KP-Sil column of 60 Å $SiO_2$ 32-63 μm (eluent: 7/3 cyclohexane/ethyl acetate, then 9/1 dichloromethane/solution A; solution A=38/17/2 dichloromethane/methanol/aqueous ammonia). 239 mg of a yellow powder of a mixture of di-Boc and tri-Boc derivatives of N-(2-{3-[4-(3-cyano-2-hydrazinopyrid-4-yl)phenyl]ureido}-4-trifluoromethylphenyl)acetamide are obtained.

N-(2-{3-[4-(3-Amino-1H-pyrazolo[3,4-b]pyrid-4-yl)phenyl]ureido}-4-trifluoromethylphenyl)acetamide Prepared According to Scheme 1

The di-Boc and tri-Boc derivatives of N-(2-{3-[4-(3-cyano-2-hydrazinopyrid-4-yl)-phenyl]ureido}-4-trifluoromethylphenyl)acetamide are converted according to the procedure for the preparation of Example 6. The product obtained is a pale yellow powder, the characteristics of which are as follows:

MS-ES⁺: 470(+)=(M+H)(+)

IR spectrum (KBr): 3363; 1672; 1596; 1525; 1435; 1336; 1316; 1126; 1078 and 825 cm⁻¹

¹H NMR spectrum (400 MHz, (CD₃)₂SO-d6, δ in ppm): 2.16 (broad s, 3H); 4.58 (s, 2H); 6.91 (d, J=5.0 Hz, 1H); 7.39 (broad d, J=9.0 Hz, 1H); from 7.52 to 7.58 (m, 3H); 7.67 (d, J=8.5 Hz, 2H); 8.21 (broad s, 1H); 8.29 (broad s, 1H); 8.37 (d, J=5.0 Hz, 1H); 9.52 (broad s, 1H); 9.84 (broad s, 1H); 12.25 (broad s, 1H).

EXAMPLE 13

N-(2-{3-[5-(3-Amino-1H-pyrazolo[3,4-b]pyrid-4-yl)pyrid-2-yl]ureido}-4-trifluoromethylphenyl)acetamide

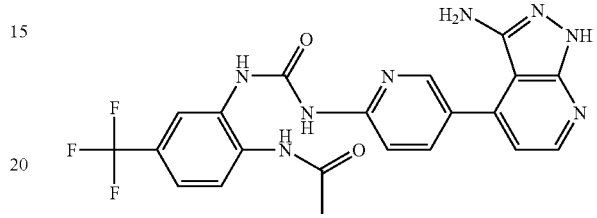

N-(2-{3-[5-(4,4,5,5-Tetramethyl-1,3,2-dioxaborolan-2-yl)pyrid-2-yl]ureido}-4-trifluoromethylphenyl)acetamide Prepared According to Scheme 4

To a solution of 10 mg of tricyclohexylphosphine in 2.5 mL of dioxane at 20° C. are added 6 mg of bis(dibenzylideneacetone)palladium. The violet-brown solution is stirred for 30 minutes. 100 mg of N-{2-[3-(5-bromopyrid-2-yl)ureido]-4-trifluoromethylphenyl}acetamide, 36 mg of potassium acetate and 84 mg of bis(pinacolato)diboron are then added. The suspension is refluxed for 3 hours 15 minutes and the suspension is then cooled to 20° C. and concentrated to dryness under reduced pressure. The green-grey residue is taken up in ethyl acetate and the insoluble material is removed by filtration. The yellow filtrate is washed with water and then dried over magnesium sulfate and concentrated under reduced pressure. 88 mg of a white-yellow powder of N-(2-{3-[5-(4,4,5,5-tetramethyl-1,3,2-dioxaborolan-2-yl)pyrid-2-yl]ureido}-4-trifluoromethylphenyl)acetamide are obtained, the characteristics of which are as follows:

MS-ES⁺: 465(+)=(M+H)(+)

4-Iodo-1H-pyrazolo[3,4-b]pyrid-3-ylamine

Prepared According to Scheme 5

To a solution of 1.145 g of 2-fluoro-4-iodonicotinonitrile in 27 ml of ethanol are added 2.5 ml of hydrazine hydrate. As soon as the hydrazine hydrate is introduced, a white precipitate forms. The suspension is stirred at 20° C. for 20 minutes. The precipitate is filtered off and washed with ethanol. 882 mg of a beige-coloured powder of 2-hydrazino-4-iodonicotinonitrile are obtained. This intermediate is taken up in 35 ml of dichloromethane. To the suspension are added 5.8 ml of trifluoroacetic acid containing 10% of anisole. The orange-yellow solution obtained is stirred at 20° C. for 30 minutes. The reaction mixture is concentrated to dryness under reduced pressure. The red powder obtained is taken up in water with 28% aqueous ammonia (in an amount sufficient to give a basic pH): the suspension turns pale yellow. The insoluble material is filtered off and dried to give 862 mg of 4-iodo-1H-pyrazolo[3,4-b]pyrid-3-ylamine.

N-(2-{3-[5-(3-Amino-1H-pyrazolo[3,4-b]pyrid-4-yl)pyrid-2-yl]ureido}-4-trifluoromethylphenyl)acetamide Prepared According to Scheme 1

To a solution of 70 mg of 4-iodo-1H-pyrazolo[3,4-b]pyrid-3-ylamine in 5.5 mL of dioxane, at 20° C., are added 246 mg of N-(2-{3-[5-(4,4,5,5-tetramethyl-1,3,2-dioxaborolan-2-yl)pyrid-2-yl]ureido}-4-trifluoromethylphenyl)acetamide. To this suspension is added a solution of 64 mg of sodium bicarbonate in 1 mL of water, followed by addition of 32 mg of tetrakis(triphenylphosphine)palladium. The reaction is refluxed at 85° C. for 3 hours 30 minutes. The pale yellow solution is cooled and ethyl acetate is then added. The mixture is washed with water. An insoluble material is isolated by filtration and the filtrate is then washed with brine. The organic phase is dried over magnesium sulfate and concentrated to dryness under reduced pressure. The yellow residue thus obtained and the preceding insoluble material are purified on a prepacked Biotage KP-Sil column of 60 Å $SiO_2$ 32-63 μm (eluent: 9/1 then 8/2 then 7/3 dichloromethane/solution A; solution A=38/17/2 dichloromethane/methanol/aqueous ammonia). 52 mg of a yellow powder of N-(2-{3-[5-(3-amino-1H-pyrazolo[3,4-b]pyrid-4-yl)pyrid-2-yl]ureido}-4-trifluoromethylphenyl)acetamide are obtained, the characteristics of which are as follows:

MS-ES$^+$: 471 (+)=(M+H)(+)
MS-ES$^-$: 469(−)=(M−H)(−)
$^1$H NMR spectrum (300 MHz, $(CD_3)_2$SO-d6, δ in ppm): 2.16 (s, 3H); 4.70 (s, 2H); 6.97 (d, J=5.0 Hz, 1H); 7.40 (d, J=9.0 Hz, 1H); from 7.47 to 7.54 (m, 2H); 8.04 (d, J=9.0 Hz, 1H); 8.41 (d, J=5.0 Hz, 1H); 8.48 to 8.54 (m, 2H); 9.86 (s, 1H); 10.15 (broad m, 1H); 10.85 (broad m, 1H); 12.35 (s, 1H).
IR spectrum (KBr): 3440; 3213; 3043; 2925; 1706; 1609; 1515; 1432; 1332; 1249; 1164; 1108; 1080 and 822 cm$^{-1}$

EXAMPLE 14

1-[4-(3-Amino-1H-pyrazolo[3,4-b]pyrid-4-yl)phenyl]-3-(2-ethoxy-5-trifluoromethylphenyl)urea

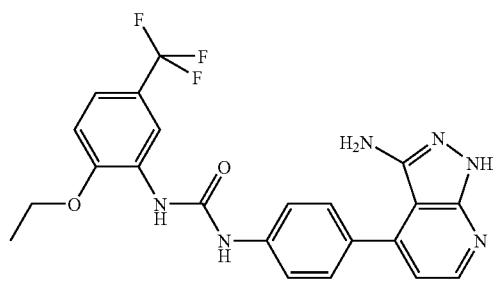

2-Ethoxy-5-trifluoromethylphenylamine was prepared according to: European Journal of Pharmaceutical Sciences 22 (2004) pp. 153-164

1-(2-Ethoxy-5-trifluoromethylphenyl)-3-[4-(4,4,5,5-tetramethyl-1,3,2-dioxaborolan-2-yl)phenyl]urea 2-Ethoxy-5-trifluoromethylphenylamine is reacted with 2-(4-isocyanatophenyl)-4,4,5,5-tetramethyl-1,3,2-dioxaborolane according to the preparation of 1-(2-methoxy-4-trifluoromethylphenyl)-3-[4-(4,4,5,5-tetramethyl-1,3,2-dioxaborolan-2-yl)phenyl]urea described in Example 5. After purification, a beige-coloured powder of 1-(2-ethoxy-5-trifluoromethylphenyl)-3-[4-(4,4,5,5-tetramethyl-1,3,2-dioxaborolan-2-yl)phenyl]urea is obtained, the characteristics of which are as follows:

MS-ES$^+$: 451 (+)=(M+H)(+)
MS-ES$^-$: 449(−)=(M−H)(−)
$^1$H NMR spectrum (300 MHz, $(CD_3)_2$SO-d6, δ in ppm): 1.28 (s, 12H); 1.45 (t, J=7.0 Hz, 3H); 4.25 (q, J=7.0 Hz, 2H); 7.18 (d, J=8.5 Hz, 1H); 7.30 (dd, J=2.5 and 8.5 Hz, 1H); 7.50 (d, J=8.5 Hz, 2H); 7.61 (d, J=8.5 Hz, 2H); 8.37 (s, 1H); 8.55 (d, J=2.5 Hz, 1H); 9.66 (s, 1H).

1-[4-(3-Amino-1H-pyrazolo[3,4-b]pyrid-4-yl)phenyl]-3-(2-ethoxy-5-trifluoromethylphenyl)urea 1-(2-Ethoxy-5-trifluoromethylphenyl)-3-[4-(4,4,5,5-tetramethyl-1,3,2-dioxaborolan-2-yl)phenyl]urea is coupled, by Suzuki reaction, with 4-iodo-1H-pyrazolo[3,4-b]pyrid-3-ylamine according to the preparation of Example 6. A yellow powder of 1-[4-(3-amino-1H-pyrazolo[3,4-b]pyrid-4-yl)phenyl]-3-(2-ethoxy-5-trifluoromethylphenyl)urea is obtained, the characteristics of which are as follows:

MS-ES$^+$: 457(+)=(M+H)(+)
IR spectrum (KBr): 3369; 1672; 1601; 1542; 1445; 1315; 1271; 1210; 1134; 1043 and 822 cm$^{-1}$
$^1$H NMR spectrum (400 MHz, $(CD_3)_2$SO-d6, δ in ppm): 1.47 (t, J=7.0 Hz, 3H); 4.27 (q, J=7.0 Hz, 2H); 4.59 (broad s, 2H); 6.91 (d, J=5.0 Hz, 1H); 7.21 (d, J=8.5 Hz, 1H); 7.31 (broad d, J=8.5 Hz, 1H); 7.55 (d, J=8.5 Hz, 2H); 7.68 (d, J=8.5 Hz, 2H); 8.36 (d, J=5.0 Hz, 1H); 8.44 (s, 1H); 8.58 (broad s, 1H); 9.78 (s, 1H); 12.25 (s, 1H).

EXAMPLE 15

1-[4-(3-Amino-1H-pyrazolo[3,4-b]pyrid-4-yl)phenyl]-3-(2-fluoro-5-methylphenyl)-urea

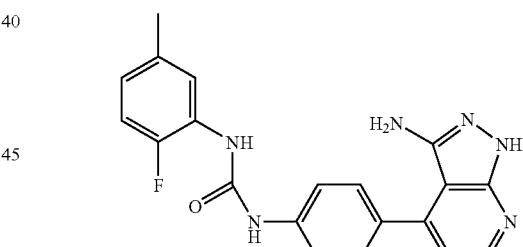

1-(2-Fluoro-5-methylphenyl)-3-[4-(4,4,5,5-tetramethyl-1,3,2-dioxaborolan-2-yl)phenyl]urea To a solution of 1.45 g of 4-(4,4,5,5-tetramethyl-[1,3,2]dioxaborolan-2-yl)-phenylamine, 1.86 mL of triethylamine and 162 mg of 4-dimethlaminopyridine in 150 mL of tetrahydrofuran at 20° C. is added 1 g of 1-fluoro-2-isocyanato-4-methylbenzene. The reaction is stirred for 3 hours 30 minutes at 60° C., and then concentrated to dryness under reduced pressure. The residue is taken up in a mixture of water and dichloromethane. The organic phase is washed with 1N HCl solution and then dried over magnesium sulfate and concentrated to dryness under reduced pressure. 2.13 g of a white powder of 1-(2-fluoro-5-methylphenyl)-3-[4-(4,4,5,5-tetramethyl-1,3,2-dioxaborolan-2-yl)phenyl]urea are obtained, the characteristics of which are as follows:

MS-EI: 370(+)=(M)(+); 125(+)=($C_7H_8NF$)(+) base peak
$^1$H NMR spectrum (400 MHz, ($CD_3$)$_2$SO-d6, δ in ppm):
1.28 (s, 12H); 2.27 (s, 3H); 6.81 (m, 1H); 7.10 (dd, J=8.5 and 11.5 Hz, 1H); 7.47 (d, J=8.5 Hz, 2H); 7.60 (d, J=8.5 Hz, 2H); 7.98 (dd, J=2.0 and 8.0 Hz, 1H); 8.51 (d, J=2.5 Hz, 1H); 9.21 (s, 1H).

1-[4-(3-Amino-1H-pyrazolo[3,4-b]Pyrid-4-yl)phenyl]-3-(2-fluoro-5-methylphenyl)-urea 1-(2-Fluoro-5-methylphenyl)-3-[4-(4,4,5,5-tetramethyl-1,3,2-dioxaborolan-2-yl)-phenyl]urea is coupled, by Suzuki reaction, with 4-bromo-1H-pyrazolo[4,3-c]pyrid-3-ylamine according to a protocol similar to that for the preparation of Example 3. A yellow powder of 1-[4-(3-amino-1H-pyrazolo[3,4-b]pyrid-4-yl)phenyl]-3-(2-fluoro-5-methylphenyl)urea is obtained, the characteristics of which are as follows:

MS-ES$^+$: 377(+)=(M+H)(+)
MS-ES$^-$: 375(−)=(M−H)(−)
$^1$H NMR spectrum (400 MHz, ($CD_3$)$_2$SO-d6, δ in ppm):
2.28 (s, 3H); 4.57 (s, 2H); 6.82 (m, 1H); 6.91 (d, J=5.0 Hz, 1H); 7.11 (dd, J=8.5 and 11.5 Hz, 1H); 7.54 (d, J=8.5 Hz, 2H); 7.65 (d, J=8.5 Hz, 2H); 7.99 (broad d, J=7.5 Hz, 1H); 8.37 (d, J=5.0 Hz, 1H); 8.56 (broad s, 1H); 9.29 (s, 1H); 12.25 (s, 1H).
IR spectrum (KBr): 3368; 1709; 1602; 1537; 1314; 1217; 1184; 1116 and 817 cm$^{-1}$

EXAMPLE 16

1-[4-(3-Amino-1H-pyrazolo[3,4-b]pyrid-4-yl)phenyl]-3-(3,4-dimethylphenyl)urea

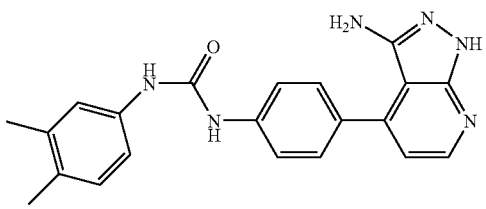

4-(4-Aminophenyl)-1H-pyrazolo[3,4-b]pyrid-3-ylamine

Prepared According to Scheme 6

To a solution of 190 mg of 4-bromo-1H-pyrazolo[4,3-c]pyrid-3-ylamine and 236 mg of 4-(4,4,5,5-tetramethyl[1,3,2]dioxaborolan-2-yl)phenylamine in 20 mL of dioxane are added a solution of 215 mg of sodium bicarbonate in 5 mL of water, and then 103 mg of tetrakis(triphenylphosphine)palladium. The reaction is heated at 85° C. for 3 hours 30 minutes. The dark yellow solution is cooled to room temperature and 30 mL of ethyl acetate are added, and the mixture is then washed with water and brine. The organic phase is dried over magnesium sulfate and evaporated to dryness under reduced pressure. The solid yellow residue is purified on a prepacked Biotage KP-Sil column of 60 Å SiO$_2$ 32-63 μm (eluent: 95/5 then 90/10 then 80/20 dichloromethane/solution A; solution A=38/17/2 dichloromethane/methanol/aqueous ammonia). 93 mg of a yellow powder of 4-(4-aminophenyl)-1H-pyrazolo[3,4-b]pyrid-3-ylamine are obtained, the characteristics of which are as follows:

MS-EI: 225(+)=(M)(+) base peak
$^1$H NMR spectrum (300 MHz, ($CD_3$)$_2$SO-d6, δ in ppm):
4.57 (broad s, 2H); 5.47 (broad s, 2H); 6.71 (d, J=8.5 Hz, 2H); 6.80 (d, J=5.0 Hz, 1H); 7.28 (d, J=8.5 Hz, 2H); 8.28 (d, J=5.0 Hz, 1H); 12.1 (broad s, 1H)

1-[4-(3-Amino-1H-pyrazolo[3,4-b]pyrid-4-yl)phenyl]-3-(3,4-dimethylphenyl)urea Prepared According to Scheme 6

To a solution of 100 mg of 4-(4-aminophenyl)-1H-pyrazolo[3,4-b]pyrid-3-ylamine, 125 μL of triethylamine and 10 mg of 4-dimethylaminopyridine in 17 mL of tetrahydrofuran at 20° C. are added 66 mg of 3,4-dimethylphenyl isocyanate. The reaction is stirred for 6 hours at 80° C., and then concentrated to dryness under reduced pressure. The residue is taken up in a mixture of water and ethyl acetate. The organic phase is dried over magnesium sulfate and then concentrated to dryness under reduced pressure. The yellow residue is purified on a prepacked Biotage KP-Sil column of 60 Å SiO$_2$ 32-63 μm (eluent: 95/5 then 90/10 then 80/20 dichloromethane/solution A; solution A=38/17/2 dichloromethane/methanol/aqueous ammonia). 29 mg of a yellow powder of 1-[4-(3-amino-1H-pyrazolo[3,4-b]pyrid-4-yl)phenyl]-3-(3,4-dimethylphenyl)urea are obtained, the characteristics of which are as follows:

LC-MS: rt=3.44 min: m/z 373: [M+H]$^+$, m/z 371: [M−H]$^-$, m/z 417: [M−H]$^-$+HCO2H, m/z 224: [M−H]$^-$—C9H10NO
MS-IE: m/z 372: [M$^+$], m/z 121: C8H10N$^+$ (base peak).
$^1$H NMR spectrum (400 MHz, ($CD_3$)$_2$SO-d6, δ in ppm):
2.16 (s, 3H); 2.20 (s, 3H); 4.59 (s, 2H); 6.90 (d, J=5.5 Hz, 1H); 7.04 (d, J=8.5 Hz, 1H); 7.20 (dd, J=2.5 and 8.5 Hz, 1H); 7.26 (d, J=2.5 Hz, 1H); 7.52 (d, J=8.5 Hz, 2H); 7.65 (d, J=8.5 Hz, 2H); 8.36 (d, J=5.5 Hz, 1H); 8.68 (s, 1H); 8.97 (s, 1H); 12.25 (s, 1H)

The products below were prepared according to Example 16 (Scheme 6):

EXAMPLE 17

1-[4-(3-Amino-1H-pyrazolo[3,4-b]pyrid-4-yl)phenyl]-3-(5-tert-butyl-2-methoxyphenyl)urea

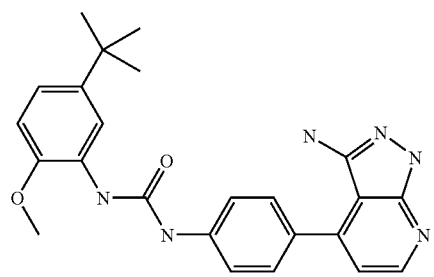

LC-MS on ZQ: rt=3.74 min: m/z 431: [M+H]$^+$, m/z 429: [M−H]$^-$ $^1$H NMR spectrum (400 MHz, ($CD_3$)$_2$SO-d6, δ in ppm):
1.28 (s, 9H); 3.87 (s, 3H); 4.59 (s, 2H); 6.90 (d, J=5.5 Hz, 1H); 6.92 (d, J=8.5 Hz, 1H); 6.97 (dd, J=2.5 and 8.5 Hz, 1H); 7.53

(d, J=8.5 Hz, 2H); 7.68 (d, J=8.5 Hz, 2H); 8.28 (m, 2H); 8.37 (d, J=5.5 Hz, 1H); 9.58 (s, 1H); 12.25 (broad s, 1H)

EXAMPLE 18

1-[4-(3-Amino-1H-pyrazolo[3,4-b]pyrid-4-yl)phenyl]-3-(4-methyl-3-trifluoromethylphenyl)urea

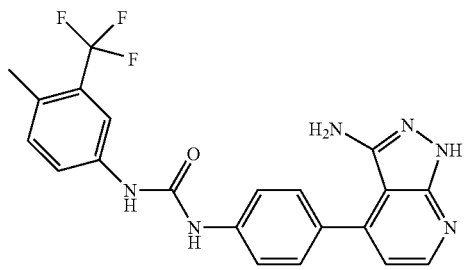

LC-MS: rt=8.84 min: m/z 427: [M+H]$^+$, m/z 425: [M–H]$^-$ $^1$H NMR spectrum (400 MHz, (CD$_3$)$_2$SO-d6, δ in ppm): 2.38 (s, 3H); 4.58 (broad s, 2H); 6.90 (d, J=5.5 Hz, 1H); 7.35 (d, J=8.5 Hz, 1H); 7.53 (m, 3H); 7.68 (d, J=8.5 Hz, 2H); 7.96 (d, J=2.5 Hz, 1H); 8.38 (d, J=5.5 Hz, 1H); 9.06 (s, 1H); 9.09 (s, 1H); 12.25 (broad s, 1H).

EXAMPLE 19

1-[4-(3-Amino-1H-pyrazolo[3,4-b]pyrid-4-yl)phenyl]-3-(3-chloro-4-methylphenyl)-urea

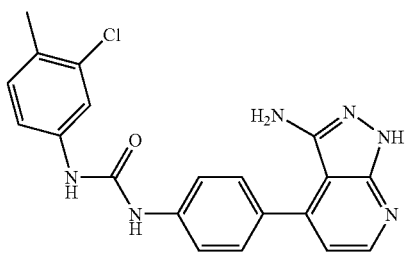

LC-MS: rt=3.30 min: m/z 393: [M+H]$^+$ (base peak), m/z 391: [M–H]$^-$ m/z 437: [M–H]$^-$+HCO2H, m/z 224: [M–H]$^-$—C8H7ClNO $^1$H NMR spectrum (300 MHz, (CD$_3$)$_2$SO-d6, δ in ppm): 2.28 (s, 3H); 4.58 (broad s, 2H); 6.90 (d, J=5.5 Hz, 1H); from 7.18 to 7.29 (m, 2H); 7.53 (d, J=8.5 Hz, 2H); 7.66 (d, J=8.5 Hz, 2H); 7.72 (broad s, 1H); 8.38 (d, J=5.5 Hz, 1H); 8.92 (s, 1H); 9.02 (s, 1H); 12.25 (broad s, 1H)

EXAMPLE 20

1-[4-(3-Amino-1H-pyrazolo[3,4-b]pyrid-4-yl)phenyl]-3-(3-ethylphenyl)urea

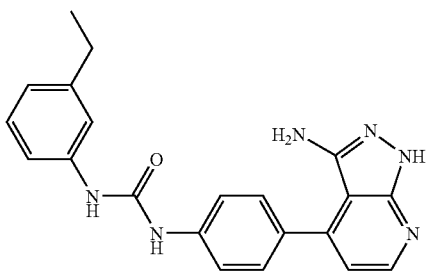

MS-ES$^+$: 373 (MH$^+$)
Retention time DAD-TIC: 3.5 min

EXAMPLE 21

1-[4-(3-Amino-1H-pyrazolo[3,4-b]pyrid-4-yl)phenyl]-3-1,3-benzodioxol-5-ylurea

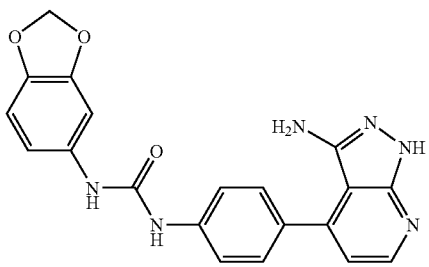

MS-ES$^+$: 389 (MH$^+$)
Retention time DAD-TIC: 2.93 min

EXAMPLE 22

1-[4-(3-Amino-1H-pyrazolo[3,4-b]pyrid-4-yl)phenyl]-3-(3-chloro-4-methoxyphenyl)urea

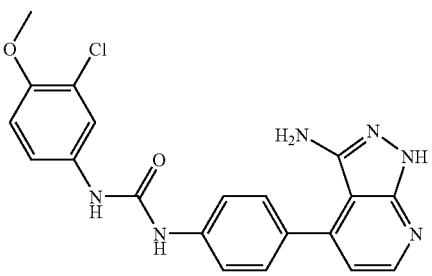

MS-ES$^+$: 409 (MH$^+$)
Retention time DAD-TIC: 3.24 min

EXAMPLE 23

1-[4-(3-Amino-1H-pyrazolo[3,4-b]pyrid-4-yl)phenyl]-3-(5-chloro-2-methoxyphenyl)urea

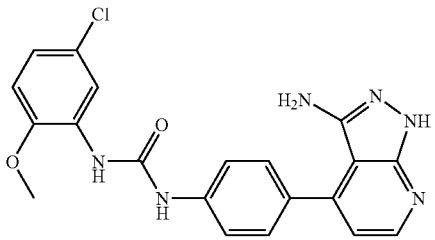

MS-ES+: 409 (MH+)
Retention time DAD-TIC: 3.62 min

EXAMPLE 24

1-[4-(3-Amino-1H-pyrazolo[3,4-b]pyrid-4-yl)phenyl]-3-(2-ethoxyphenyl)urea

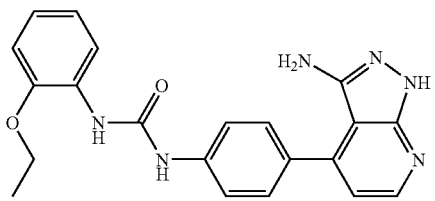

MS-ES+: 389 (MH+)
Retention time DAD-TIC: 3.44 min

EXAMPLE 25

1-[4-(3-Amino-1H-pyrazolo[3,4-b]pyrid-4-yl)phenyl]-3-(2-methoxy-5-methylphenyl)urea

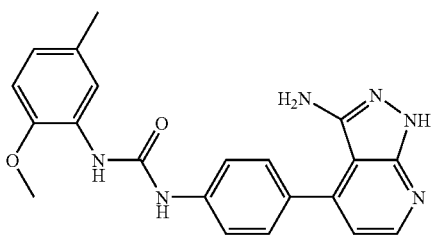

MS-ES+: 389 (MH+)
Retention time DAD-TIC: 3.4 min

EXAMPLE 26

N-[4-(3-Amino-1H-pyrazolo[3,4-b]pyrid-4-yl)phenyl]-2,3-dichlorobenzenesulfonamide

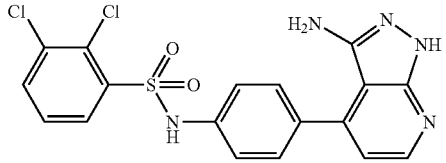

MS-ES+: 434 (MH+)
Retention time DAD-TIC:

EXAMPLE 27

1-[4-(3-Amino-1H-pyrazolo[4,3-c]pyrid-4-yl)phenyl]-3-(2-fluoro-5-methylphenyl-)urea

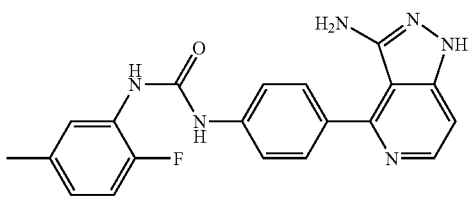

2,4-dichloronicotinonitrile

A solution of 5.0 g of commercial 4-methoxy-2-oxo-1,2-dihydropyridine-3-carbonitrile in 50 ml of phosphorus oxychloride is refluxed for 19 hours. After cooling, the reaction medium is poured into a mixture of water and ice. The precipitate formed is filtered off and the filtrate is extracted twice with a 90/10 ethyl acetate/methanol solution. The combined organic phases and the precipitate are dried over magnesium sulfate and then concentrated under reduced pressure to give 6.76 g of a yellowish powder. The crude product is purified on a prepacked Biotage KP-Sil column of 60 Å SiO$_2$ 32-63 μM (5/95 to 10/90 gradient ethyl acetate in cyclohexane) to give 2.08 g of a white powder of 2,4-dichloronicotinonitrile.

MS-IE: 172=[M+] (base peak), 137=[M+]-Cl
IR spectrum (KBr): 3072; 2236; 1559; 1539; 1445; 1368; 1220; 1197; 1069; 859; 818; 791 and 416 cm$^{-1}$
$^1$H NMR spectrum (400 MHz, (CD$_3$)$_2$SO, δ in ppm): 7.92 (d, J=5.5 Hz, 1H); 8.67 (d, J=5.5 Hz, 1H)

[4-(4-Chloro-3-cyanopyrid-2-yl)phenyl]carbamic acid tert-butyl ester

To a solution of 519 mg of 2,4-dichloronicotinonitrile in 25.5 ml of dioxane are added 782 mg of (4-boc-aminophenyl)boronic acid, 693 mg of sodium bicarbonate in 8.5 ml of water and 347 mg of tetrakis(triphenyl-phosphine)palladium. The suspension is stirred at 100° C. for 2 hours under argon. After cooling, the reaction mixture is poured into water and extracted three times with a 90/10 ethyl acetate/methanol solution. The combined organic phases are dried over magnesium sulfate and concentrated under reduced pressure. 1.58 g of crude product are chromatographed on a prepacked Biotage KP-Sil column of 60 Å SiO2 32-63 μm (from 0.5/99.5 to 1/99 gradient of solution A in dichloromethane; solution A=38/17/2 dichloromethane/methanol/aqueous ammonia). 797 mg of [4-(4-chloro-3-cyanopyrid-2-yl)phenyl]carbamic acid tert-butyl ester are obtained, the characteristics of which are as follows:

MS-EI: 329 (+)

IR spectrum (CCl$_4$): 3343; 2981; 2230; 1741; 1524; 1501; 1411; 1392; 1368; 1316; 1220; 1155; 1050 and 844 cm$^{-1}$ $^1$H NMR spectrum (400 MHz, (CD$_3$)$_2$SO, δ in ppm): 1.50 (s, 9H); 7.62 (d, J=9.0 Hz, 2H); from 7.78 to 7.84 (m, 3H); 8.83 (d, J=5.5 Hz, 1H); 9.67 (s, 1H).

2-(4-Aminophenyl)-4-chloronicotinonitrile

To a solution of 3.40 g of [4-(4-chloro-3-cyanopyrid-2-yl)phenyl]carbamic acid tert-butyl ester in 20 ml of dichloromethane are added 5.5 ml of trifluoroacetic acid. The solution is stirred at 20° C. for 26 hours. The solution is concentrated to dryness under reduced pressure. The residue is taken up in aqueous sodium bicarbonate solution and extracted three times with dichloromethane. The combined organic phases are dried over magnesium sulfate and concentrated under reduced pressure. The residue is washed with diethyl ether. 1.678 g of a yellow powder of 2-(4-aminophenyl)-4-chloronicotinonitrile are obtained, the characteristics of which are as follows:

MS-ES$^+$: 230 (+)=(M+H)(+)

IR spectrum (KBr): 3402; 3339; 3230; 2223; 1608; 1555; 1538; 1520; 1432; 1388; 1180; 1066; 825 and 607 cm$^{-1}$ $^1$H NMR spectrum (400 MHz, (CD$_3$)$_2$SO, δ in ppm): 5.76 (broad s, 2H); 6.67 (d, J=8.5 Hz, 2H); 7.63 (d, J=5.5 Hz, 1H); 7.68 (d, J=8.5 Hz, 2H); 8.73 (d, J=5.5 Hz, 1H).

1-[4-(4-Chloro-3-cyanopyrid-2-yl)phenyl]-3-(2-fluoro-5-methylphenyl)urea

Prepared According to Scheme 7

To a solution of 115 mg of 2-(4-aminophenyl)-4-chloronicotinonitrile and 70 μL of triethylamine in 5 mL of tetrahydrofuran at 20° C. are added 65 μL of 2-fluoro-5-methylphenyl isocyanate. After 3 hours at 20° C., water is added and the mixture is extracted with ethyl acetate. The organic phase is washed with water and then with brine, dried over magnesium sulfate and then concentrated to dryness under reduced pressure. The residue is taken up in ethyl ether and the insoluble material is isolated by filtration to give 118 mg of a white powder of 1-[4-(4-chloro-3-cyanopyrid-2-yl)phenyl]-3-(2-fluoro-5-methylphenyl)urea, the characteristics of which are as follows:

MS-EI: 380(+)=(M)(+); 125(+)=(C$_7$H$_8$NF)(+) base peak

IR spectrum (KBr): 3379; 2231; 1687; 1598; 1550; 1413; 1315; 1219; 1185; 1116 and 810 cm$^{-1}$ $^1$H NMR spectrum (400 MHz, (CD$_3$)$_2$SO-d6, δ in ppm): 2.28 (s, 3H); 6.82 (m, 1H); 7.12 (dd, J=8.5 and 11.5 Hz, 1H); 7.64 (d, J=8.5 Hz, 2H); 7.81 (d, J=5.5 Hz, 1H); 7.87 (d, J=8.5 Hz, 2H); 7.99 (broad d, J=8.0 Hz, 1H); 8.60 (broad s, 1H); 8.84 (d, J=5.5 Hz, 1H); 9.38 (s, 1H).

1-[4-(3-Cyano-4-hydrazinopyrid-2-yl)phenyl]-3-(2-fluoro-5-methylphenyl)urea

Prepared According to Scheme 7

To a mixture of 50 mg of 1-[4-(4-chloro-3-cyanopyrid-2-yl)phenyl]-3-(2-fluoro-5-methylphenyl)urea in 0.5 mL of ethanol at 20° C. are added 45 μL of hydrazine hydrate. The white suspension is stirred for 2 hours at 20° C. and then heated at 80° C. for 4 h. The mixture is allowed to cool to 20° C. The insoluble material is isolated by filtration and washed with ethyl ether to give 33 mg of a beige-coloured solid of 1-[4-(3-cyano-4-hydrazinopyrid-2-yl)phenyl]-3-(2-fluoro-5-methylphenyl)urea, the characteristics of which are as follows:

MS-ES$^+$: 377(+)=(M+H)(+)

MS-ES$^-$: 375(−)=(M−H)(−)

IR spectrum (KBr): 3379; 2212; 1700; 1599; 1551; 1440; 1314; 1257; 1221; 1187 and 816 cm$^{-1}$ $^1$H NMR spectrum (400 MHz, (CD$_3$)$_2$SO-d6, δ in ppm): 2.28 (s, 3H); 4.52 (s, 2H); 6.81 (m, 1H); 7.06 (d, J=6.0 Hz, 1H); 7.11 (dd, J=8.5 and 11.5 Hz, 1H); 7.57 (d, J=8.5 Hz, 2H); 7.71 (d, J=8.5 Hz, 2H); 8.00 (broad d, J=8.0 Hz, 1H); 8.24 (broad s, 1H); 8.27 (d, J=6.0 Hz, 1H); 8.57 (broad s, 1H); 9.32 (s, 1H).

1-[4-(3-Amino-1H-pyrazolo[4,3-c]pyrid-4-yl)phenyl]-3-(2-fluoro-5-methylphenyl)urea Prepared According to Scheme 7

To a solution of 55 mg of 1-[4-(3-cyano-4-hydrazinopyrid-2-yl)phenyl]-3-(2-fluoro-5-methylphenyl)urea in 2.2 mL of dichloromethane at 20° C. is added 0.25 mL of trifluoroacetic acid containing 10% of anisole. After 40 minutes, the solution is evaporated to dryness under reduced pressure. The residue is taken up in water and the medium is made basic. The precipitate formed is isolated by filtration. This beige-coloured solid is chromatographed on an AIT cartridge of 2 g of silica 15-40 μm after deposition of solid (eluting with a gradient of from 100% CH$_2$Cl$_2$ to 60% CH$_2$Cl$_2$/40% (CH$_2$Cl$_2$ 38/MeOH 17/NH$_4$OH 3). 26 mg of a beige-coloured solid of 1-[4-(3-amino-1H-pyrazolo[4,3-c]pyrid-4-yl)phenyl]-3-(2-fluoro-5-methylphenyl)urea are obtained, the characteristics of which are as follows:

m.p.: 195° C.

MS-ES$^+$: 377(+)=(M+H)(+)

IR spectrum (KBr): 3351; 1696; 1605; 1544; 1313; 1257; 1221; 1181; 1045 and 808 cm$^{-1}$ $^1$H NMR spectrum (300 MHz, (CD$_3$)$_2$SO-d6, δ in ppm): 2.28 (s, 3H); 4.73 (s, 2H); 6.82 (m, 1H); 7.12 (dd, J=8.5 and 11.5 Hz, 1H); 7.19 (d, J=6.0 Hz, 1H); from 7.59 to 7.67 (m, 4H); 8.01 (dd, J=2.5 and 8.0 Hz, 1H); 8.21 (d, J=6.0 Hz, 1H); 8.55 (d, J=2.5 Hz, 1H); 9.26 (s, 1H); 12.1 (broad s, 1H).

The products below were prepared according to a protocol similar to that of Example 27 (Scheme 7).

EXAMPLE 28

1-[4-(3-amino-1H-pyrazolo[4,3-c]pyrid-4-yl)phenyl]-3-(2,4-dimethoxyphenyl)urea

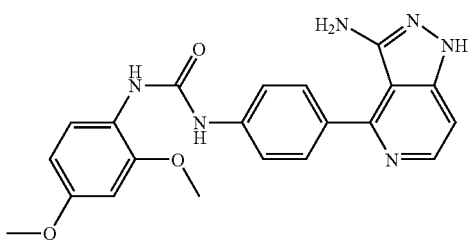

1-[4-(4-Chloro-3-cyanopyrid-2-yl)phenyl]-3-(2,4-dimethoxyphenyl)urea

Prepared According to Scheme 7

2-(4-Aminophenyl)-4-chloronicotinonitrile is reacted with 2,4-dimethoxyphenyl isocyanate under conditions similar to those described in Example 27. 1-[4-(4-Chloro-3-cyanopyrid-2-yl)phenyl]-3-(2,4-dimethoxyphenyl)urea is obtained in the form of a white solid, the characteristics of which are as follows:

MS-ES$^+$: 409(+)=(M+H)(+)

$^1$H NMR spectrum (400 MHz, (CD$_3$)$_2$SO-d6, δ in ppm): 3.74 (s, 3H); 3.88 (s, 3H); 6.50 (dd, J=2.5 and 9.0 Hz, 1H); 6.63 (d, J=2.5 Hz, 1H); 7.62 (d, J=8.5 Hz, 2H); 7.80 (d, J=5.5 Hz, 1H); 7.85 (d, J=8.5 Hz, 2H); 7.94 (d, J=9.0 Hz, 1H); 8.12 (s, 1H); 8.84 (d, J=5.5 Hz, 1H); 9.49 (s, 1H).

1-[4-(3-Amino-1H-pyrazolo[4,3-c]pyrid-4-yl)phenyl]-3-(2,4-dimethoxyphenyl)urea Prepared According to Scheme 7

1-[4-(4-Chloro-3-cyanopyrid-2-yl)phenyl]-3-(2,4-dimethoxyphenyl)urea is treated with hydrazine hydrate and then with trifluoroacetic acid under conditions similar to those described in Example 27. 1-[4-(3-Amino-1H-pyrazolo[4,3-c]pyrid-4-yl)phenyl]-3-(2,4-dimethoxyphenyl)urea is obtained in the form of a beige-coloured solid, the characteristics of which are as follows:

MS-ES$^+$: 405(+)=(M+H)(+)

IR spectrum (KBr): 1603; 1526; 1452; 1210; 1180; 1157; 1035 and 824 cm$^{-1}$ $^1$H NMR spectrum (300 MHz, (CD$_3$)$_2$SO-d6, δ in ppm): 3.74 (s, 3H); 3.87 (s, 3H); 4.74 (broad s, 2H); 6.50 (dd, J=2.5 and 9.0 Hz, 1H); 6.63 (d, J=2.5 Hz, 1H); 7.18 (d, J=6.0 Hz, 1H); 7.61 (broad s, 4H); 7.95 (d, J=9.0 Hz, 1H); 8.09 (s, 1H); 8.20 (d, J=6.0 Hz, 1H); 9.39 (broad s, 1H); 12.1 (broad m, 1H)

EXAMPLE 29

1-[4-(3-Amino-1H-pyrazolo[4,3-c]pyrid-4-yl)phenyl]-3-(5-tert-butyl-2-methoxyphenyl)urea

JK33913-110-1

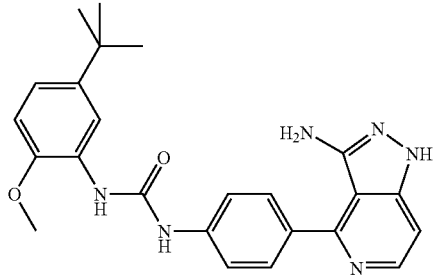

The product is a yellow solid, the characteristics of which are as follows:

LC-MS: 431 (+)=(M+H)(+)
m.p.=181° C. (Köfler)

IR spectrum (KBr): 3333; 2958; 1678; 1604; 1525; 1487; 1421; 1315; 1249; 1216; 1177; 1143; 1042; 842 and 807 cm$^{-1}$ $^1$H NMR spectrum (300 MHz, (CD$_3$)$_2$SO-d6, δ in ppm): 1.27 (s, 9H); 3.87 (s, 3H); 4.73 (broad s, 2H); 6.92 (d, J=8.5 Hz, 1H); 6.97 (dd, J=2.0 and 8.5 Hz, 1H); 7.19 (d, J=6.0 Hz, 1H); 7.63 (s, 4H); 8.21 (d, J=6.0 Hz, 1H); 8.25 (s, 1H); 8.29 (d, J=2.5 Hz, 1H); 9.51 (s, 1H); 12.1 (broad s, 1H).

EXAMPLE 30

1-[4-(3-Amino-1H-pyrazolo[4,3-c]pyrid-4-yl)phenyl]-3-(3,4-dimethylphenyl)urea

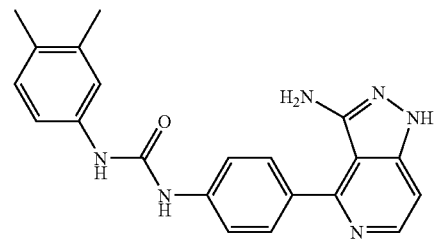

The product is a yellow solid, the characteristics of which are as follows:

MS-ES$^+$:

IR spectrum (KBr): 3413; 1679; 1621; 1549; 1210; 1136; 842; 803 and 724 cm$^{-1}$ contains trifluoroacetic acid $^1$H NMR spectrum (400 MHz, (CD$_3$)$_2$SO-d6, δ in ppm): 2.16 (s, 3H); 2.20 (s, 3H); 4.74 (broad s, 2H); 7.04 (d, J=8.0 Hz, 1H); 7.18 (d, J=6.0 Hz, 1H); 7.20 (partially masked d, J=2.5 and 8.5 Hz, 1H); 7.26 (d, J=2.5 Hz, 1H); 7.62 (s, 4H); 8.21 (d, J=6.0 Hz, 1H); 8.60 (s, 1H); 8.87 (s, 1H); 12.15 (s, 1H)

EXAMPLE 31

1-[4-(3-Amino-1H-pyrazolo[4,3-c]pyrid-4-yl)phenyl]-3-(4-methyl-3-trifluoromethylphenyl)urea

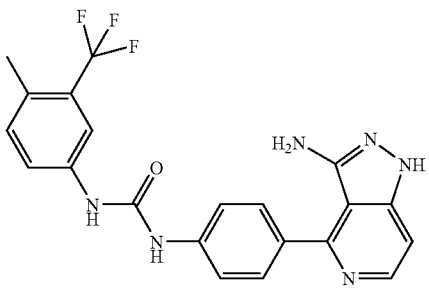

The product is a yellow solid, the characteristics of which are as follows:

MS-ES$^+$:

IR spectrum (KBr): 3393; 3319; 3226; 3112; 1678; 1621; 1552; 1529; 1505; 1319; 1206; 1186; 1134; 1054; 839; 802 and 723 cm$^{-1}$ contains trifluoroacetic acid $^1$H NMR spectrum (400 MHz, (CD$_3$)$_2$SO-d6, δ in ppm): 2.38 (q, J=2.0 Hz, 3H); 4.74 (broad s, 2H); 7.19 (d, J=6.0 Hz, 1H); 7.35 (d, J=8.5 Hz, 1H); 7.53 (dd, J=2.5 and 8.5 Hz, 1H);

7.64 (s, 4H); 7.96 (d, J=2.5 Hz, 1H); 8.21 (d, J=6.0 Hz, 1H); 8.96 (s, 1H); 9.00 (s, 1H); 12.15 (s, 1H)

EXAMPLE 32

1-[4-(3-Amino-1H-pyrazolo[4,3-c]pyrid-4-yl)phenyl]-3-(2,5-difluorophenyl)urea

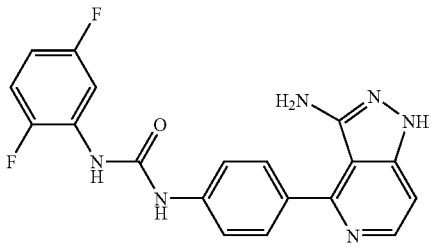

The product is a yellow solid, the characteristics of which are as follows:

LC-MS: 381(+)=(M+H)(+)

m.p.=187° C. (Köfler)

IR spectrum (KBr): 3372; 1718; 1606; 1534; 1442; 1313; 1208; 1179; 862; 796 and 727 cm$^{-1}$ $^1$H NMR spectrum (300 MHz, (CD$_3$)$_2$SO-d6, δ in ppm): 4.74 (broad s, 2H); 6.84 (m, 1H); 7.20 (d, J=6.0 Hz, 1H); 7.31 (ddd, J=5.5-9.0 and 11.0 Hz, 1H); from 7.61 to 7.68 (m, 4H); 8.07 (ddd, J=3.0-6.5 and 11.0 Hz, 1H); 8.21 (d, J=6.0 Hz, 1H); 8.87 (broad s, 1H); 9.36 (s, 1H); 12.15 (broad s, 1H).

EXAMPLE 33

1-[4-(3-Amino-1H-pyrazolo[4,3-c]pyrid-4-yl)phenyl]-3-(3-chloro-4-methylphenyl)-urea

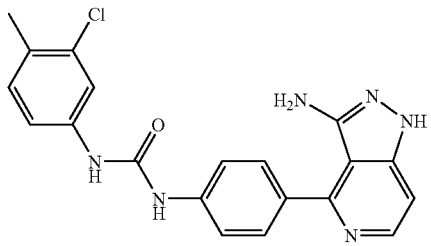

The product is a pale yellow solid, the characteristics of which are as follows:

MS-ES$^+$:

IR spectrum (KBr): 3406; 3323; 3110; 1675; 1621; 1592; 1528; 1498; 1210; 1185; 1139; 839; 803 and 724 cm$^{-1}$ contains trifluoroacetic acid $^1$H NMR spectrum (400 MHz, (CD$_3$)$_2$SO-d6, δ in ppm): 2.27 (s, 3H); 4.74 (broad s, 2H); 7.19 (d, J=5.5 Hz, 1H); 7.21 (dd, J=2.0 and 8.5 Hz, 1H); 7.25 (d, J=2.0 Hz, 1H); 7.63 (s, 4H); 7.72 (d, J=2.5 Hz, 1H); 8.21 (d, J=5.5 Hz, 1H); 8.88 (s, 1H); 8.96 (s, 1H); 12.15 (s, 1H).

EXAMPLE 34

1-[4-(3-Amino-1H-pyrazolo[4,3-c]pyrid-4-yl)phenyl]-3-(5-fluoro-2-methylphenyl)urea

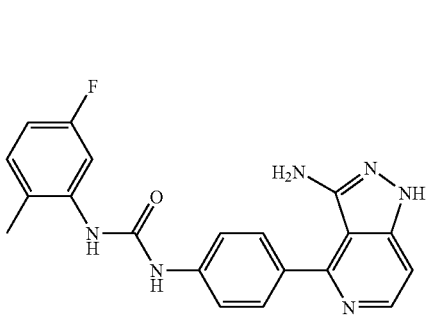

The product is a yellow solid, the characteristics of which are as follows:

LC-MS: 377(+)=(M+H)(+)

m.p.=>265° C. (Köfler)

IR spectrum (KBr): 3287; 1639; 1604; 1539; 1452; 1312; 1217; 1156; 1109; 1046; 846 and 809 cm$^{-1}$ $^1$H NMR spectrum (300 MHz, (CD$_3$)$_2$SO-d6, δ in ppm): 2.24 (s, 3H); 4.74 (broad s, 2H); 6.76 (dt, J=3.0 and 8.5 Hz, 1H); 7.19 (d, J=6.0 Hz, 1H); 7.20 (partially masked m, 1H); 7.64 (s, 4H); 7.86 (dd, J=3.0 and 12.0 Hz, 1H); 8.15 (broad s, 1H); 8.21 (d, J=6.0 Hz, 1H); 9.40 (broad s, 1H); 12.15 (broad s, 1H).

EXAMPLE 35

N-[4-(3-Amino-1H-pyrazolo[4,3-c]pyrid-4-yl)phenyl]-2,3-dichlorobenzenesulfonamide

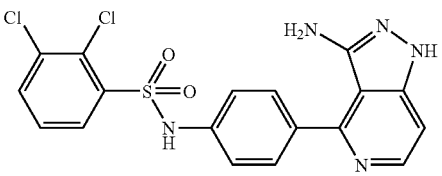

MS-ES$^+$: 434 (MH$^+$)

EXAMPLE 36

1-[4-(3-Amino-1H-pyrazolo[4,3-c]pyrid-4-yl)phenyl]-3-(5-chloro-2,4-dimethoxyphenyl)urea

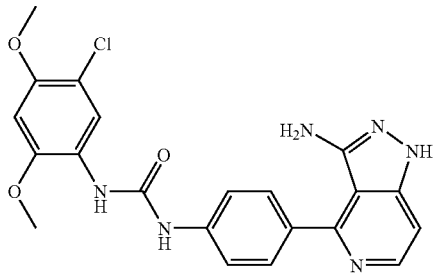

MS-ES+: 439 (MH+)

EXAMPLE 37

1-[4-(3-Amino-1H-pyrazolo[4,3-c]pyrid-4-yl)phenyl]-3-(3-trifluoromethyl-sulfanylphenyl)urea

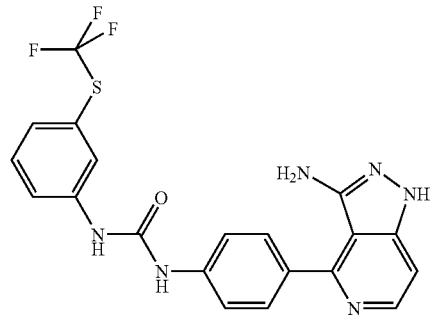

MS-ES+: 445 (MH+)

EXAMPLE 38

1-[4-(3-Amino-1H-pyrazolo[3,4-c]pyrid-4-yl)phenyl]-3-(2-methoxy-5-trifluoromethylphenyl]urea

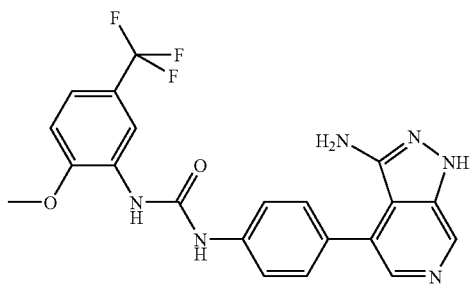

3-Chloro-5-(4-nitrophenyl)isonicotinonitrile

Prepared According to Scheme 8

To a solution of 1.73 g of commercial 3,5-dichloroisonicotinonitrile in 120 ml of dioxane are added 2.74 g of 4,4,5,5-tetramethyl-2-(4-nitrophenyl)-1,3,2-dioxaborolane, 2.31 g of sodium bicarbonate in 70 ml of water and 1.16 g of tetrakis(triphenylphosphine)palladium (0). The suspension is heated at 100° C. for 1 hour 30 minutes. After cooling, the reaction mixture is poured into 40 ml of water and extracted with three times 100 ml of ethyl acetate. The combined organic phases are washed with 50 ml of water, 50 ml of brine, dried over magnesium sulfate and concentrated to dryness under reduced pressure. The residual brown gum is purified by chromatography on a prepacked Merck cartridge of 70 g of silica 15-40 µm, eluting with dichloromethane. 1.58 g of a yellow solid of 3-chloro-5-(4-nitrophenyl)isonicotinonitrile are obtained, the characteristics of which are as follows:

MS-EI: 259 (+)

$^1$H NMR spectrum (400 MHz, $(CD_3)_2SO$, δ in ppm): 8.02 (d, J=9.0 Hz, 2H); 8.43 (d, J=9.0 Hz, 2H); 8.91 (s, 1H); 9.09 (s, 1H)

N,N'-Di-Boc derivative of 3-hydrazino-5-(4-nitrophenyl)isonicotinonitrile

Prepared According to Scheme 8

To a solution of 4.43 g of di-tert-butyl hydrazinodiformate in 19 ml of dimethylformamide are added 2.62 g of potassium carbonate and 990 mg of 3-chloro-5-(4-nitrophenyl)isonicotinonitrile. The suspension is heated at 75° C. for 6 hours and then stirred for 18 hours at 20° C. The reaction mixture is extracted with 3 times 80 ml of ethyl acetate. The organic phases are washed with twice 50 ml of water and then with 50 ml of brine. The combined organic phases are dried over magnesium sulfate and concentrated under reduced pressure. The brown residue is purified by chromatography on a prepacked Merck cartridge of 25 g of silica 15-40 µm (elution gradient: 9/1 to 7/3 cyclohexane/ethyl acetate). 2.38 g of a yellow solid of the N,N'-di-Boc derivative of 3-hydrazino-5-(4-nitrophenyl)isonicotinonitrile are obtained, which are isolated in impure form and used without further purification.

LC-MS: 456 (+)=(M+H) (+)
454 (−)=(M−H) (−)

N,N'-Di-Boc derivative of 3-(4-aminophenyl)-5-hydrazinoisonicotinonitrile

Prepared According to Scheme 8

To a solution of 1.74 g of the N,N'-di-Boc derivative of 3-hydrazino-5-(4-nitrophenyl)isonicotinonitrile in 8 ml of ethanol are added 3 ml of cyclohexene and 200 mg of palladium hydroxide. The suspension is refluxed for 2 hours 15 minutes with stirring, filtered while hot through Celite and concentrated to dryness under reduced pressure. The beige-coloured residue is purified by chromatography on a Merck cartridge of 70 g of silica 15-40 µm, eluting with an 8/2 ethyl acetate/dichloromethane solution. 309 mg of a yellow solid of the N,N'-di-Boc derivative of 3-(4-aminophenyl)-5-hydrazinoisonicotinonitrile are obtained, the characteristics of which are as follows:

LC-MS: 426 (+)=(M+H) (+)

$^1$H NMR spectrum (400 MHz, $(CD_3)_2SO$, δ in ppm): 1.45 (broad s, 18H); 5.61 (s.2H); 6.71 (d, J=9.0 Hz, 2H); 7.31 (d, J=9.0 Hz, 2H); 8.55 (broad s, 1H); 8.64 (s, 1H); 10.05 (broad m, 1H)

N,N' di-Boc derivative of 1-[4-(4-cyano-5-hydrazinopyrid-3-yl)phenyl]-3-(2-methoxy-5-trifluoromethylphenyl]urea Prepared According to Scheme 8

To a solution of 41 mg of triphosgene in 4 ml of tetrahydrofuran are added, at 0° C. under argon, 78 mg of 2-methoxy-5-trifluoromethyl aniline in 2 ml of tetrahydrofuran and 110 μl of triethylamine. The suspension is stirred at 0° C. for 10 minutes and then at 20° C. for 1 hour 15 minutes. A solution of 174 mg of the N,N'-di-Boc derivative of 3-(4-aminophenyl)-5-hydrazinoisonicotinonitrile in 2 ml of tetrahydrofuran is then added. The reaction mixture is refluxed for 8 hours and then concentrated to dryness under reduced pressure. The residue is purified by chromatography on an Analogix cartridge of 12 g of silica 50 μm (1/9 to 5/5 elution gradient of ethyl acetate in cyclohexane). 195 mg of a yellow solid of the N,N'-di-Boc derivative of 1-[4-(4-cyano-5-hydrazinopyrid-3-yl)phenyl]-3-(2-methoxy-5-trifluoromethylphenyl]urea are obtained, the characteristics of which are as follows:

LC-MS: 643 (+)=(M+H) (+)

$^1$H NMR spectrum (400 MHz, (CD$_3$)$_2$SO, δ in ppm): From 1.4 to 1.55 (broad s, 18H); 3.99 (s, 3H); 7.22 (d, J=8.5 Hz, 1H); 7.34 (dd, J=2.0 and 8.5 Hz, 1H); 7.58 (d, J=9.0 Hz, 2H); 7.69 (d, J=9.0 Hz, 2H); 8.57 (d, J=2.0 Hz, 1H); 8.65 (s, 1H); 8.69 (broad s, 1H); 8.72 (s, 1H); 9.78 (s, 1H); 10.08 (broad m, 1H)

1-[4-(3-Amino-1H-pyrazolo[3,4-c]pyrid-4-yl)phenyl]-3-(2-methoxy-5-trifluoromethylphenyl]urea Prepared According to Scheme 8

A solution of 282 mg of the N,N'-di-Boc derivative of 1-[4-(4-cyano-5-hydrazinopyrid-3-yl)phenyl]-3-(2-methoxy-5-trifluoromethylphenyl]urea and 600 μl of trifluoroacetic acid containing 10% of anisole in 8 ml of dichloromethane is refluxed for 2 hours 30 minutes. After cooling, the reaction mixture is poured into saturated sodium bicarbonate solution and extracted with 40 ml of ethyl acetate. The organic phase is dried over magnesium sulfate and concentrated to dryness under reduced pressure. The yellow residue is slurried in ethyl ether. After filtering off and drying the insoluble material under vacuum, 103 mg of a yellow solid of 1-[4-(3-amino-1H-pyrazolo[3,4-c]pyrid-4-yl)phenyl]-3-(2-methoxy-5-trifluoromethylphenyl]urea are obtained, the characteristics of which are as follows:

LC-MS: rt=2.83 min: 443=[M+H]$^+$; 441=[M-H]$^-$; 487=[M-H]$^-$+HCO$_2$H

MS-EI: 176 (base peak)=C$_8$H$_6$F$_3$O$^+$; 442=[M$^+$]

IR spectrum (KBr): 3342; 1696; 1609; 1538; 1491; 1447; 1314; 1270; 1215; 1177; 1135; 1024; 837 and 622 cm$^{-1}$ $^1$H NMR spectrum (400 MHz, (CD$_3$)$_2$SO, δ in ppm): 3.99 (s, 3H); 4.61 (s, 2H); 7.22 (d, J=8.5 Hz, 1H); 7.33 (broad d, J=8.5 Hz, 1H); 7.50 (d, J=8.5 Hz, 2H); 7.64 (d, J=8.5 Hz, 2H); 7.93 (s, 1H); 8.58 (broad s, 2H); 8.74 (s, 1H); 9.61 (s, 1H); 12.25 (s, 1H)

m.p.=210° C. (Köfler)

EXAMPLE 39

N-[4-(3-Amino-1H-pyrazolo[3,4-c]pyrid-4-yl)phenyl]-2,3-dichlorobenzenesulfonamide Prepared According to Schemes 6 and 8

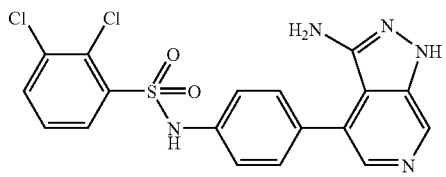

MS-ES$^+$=434 (MH$^+$)

EXAMPLE 40

3-{3-[4-(3-Amino-1H-pyrazolo[3,4-b]pyrid-4-yl)phenyl]ureido}-4-methoxy-benzoic acid

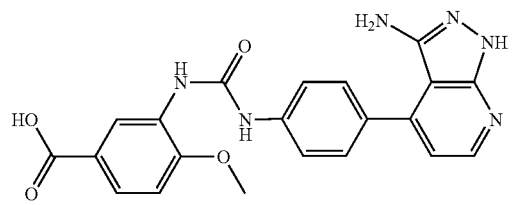

To a solution of 100 mg of 1-[4-(3-amino-1H-pyrazolo[3,4-b]pyrid-4-yl)phenyl]-3-(2-methoxy-5-trifluoromethylphenyl)urea, described in Example 5, in 5 mL of dichloromethane at −40° C. are added dropwise 1.6 mL of 1M boron tribromide solution and the temperature is allowed to return to 20° C. The mixture is concentrated to dryness under a stream of argon overnight. The residue is purified on a prepacked Biotage KP-Sil column of 60 Å SiO$_2$ 32-63 μm (eluent: 95/5 then 90/10 then 80/20 then 70/30 dichloromethane/solution A; solution A=38/17/2 dichloromethane/methanol/aqueous ammonia). 41 mg of a yellow powder of 3-{3-[4-(3-amino-1H-pyrazolo[3,4-b]pyrid-4-yl)phenyl]ureido}-4-methoxy-benzoic acid are obtained, the characteristics of which are as follows:

LC-MS on Quattro Premier: rt=5.04 min m/z 419: [M+H]$^+$

IR spectrum (KBr): 3354; 1697; 1597; 1542; 1431; 1319; 1279; 1205; 1122; 821 and 767 cm$^{-1}$ $^1$H NMR spectrum (400 MHz, (CD$_3$)$_2$SO, δ in ppm): 3.80 (s, 3H); 4.59 (s, 2H); 6.90 (d, J=5.5 Hz, 1H); 6.92 (d, J=8.5 Hz, 1H); 7.51 (dd, J=2.5 and 8.5 Hz, 1H); 7.54 (d, J=8.5 Hz, 2H); 7.67 (d, J=8.5 Hz, 2H); 8.38 (d, J=5.5 Hz, 1H); 8.40 (s, 1H); 8.79 (d, J=2.5 Hz, 1H); 9.60 (s, 1H); 10.6 (very broad m, 1H); 12.25 (broad s, 1H).

EXAMPLE 41

1-[4-(3-Amino-1H-pyrazolo[3,4-b]pyrid-4-yl)phenyl]-3-(2-hydroxy-5-trifluoromethylphenyl)urea

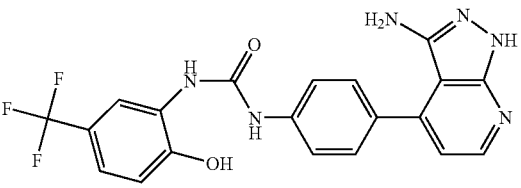

To a solution of 1-[4-(3-amino-1H-pyrazolo[3,4-b]pyrid-4-yl)phenyl]-3-(2-methoxy-5-trifluoromethylphenyl)urea, described in Example 5, in 6 mL of dichloromethane at −40° C. are added dropwise 1.6 mL of 1M boron tribromide solution, and the temperature is allowed to return to 20° C. After 30 minutes, the reaction is cooled on an ice bath and water is then added. After stirring for 15 minutes, the mixture is filtered off and the insoluble orange material is washed with water and with dichloromethane. The solid is purified on a prepacked Biotage KP-Sil column of 60 Å SiO$_2$ 32-63 µm (eluent: 95/5 then 90/10 then 80/20 then 70/30 dichloromethane/solution A; solution A=38/17/2 dichloromethane/methanol/aqueous ammonia). 29 mg of a yellow powder of 1-[4-(3-Amino-1H-pyrazolo[3,4-b]pyrid-4-yl)phenyl]-3-(2-hydroxy-5-trifluoromethylphenyl)urea are obtained, the characteristics of which are as follows:

LC-MS on ZQ: rt=3.22 nm m/z 429 [M+H]$^+$ (base peak)

$^1$H NMR spectrum (300 MHz, (CD$_3$)$_2$SO-d6, δ in ppm): 4.59 (s, 2H); 6.90 (d, J=5.5 Hz, 1H); 7.00 (d, J=8.5 Hz, 1H); 7.18 (dd, J=2.5 and 8.5 Hz, 1H); 7.54 (d, J=8.5 Hz, 2H); 7.66 (d, J=8.5 Hz, 2H); 8.37 (d, J=5.5 Hz, 1H); 8.51 (m, 2H); 9.64 (s, 1H); 10.7 (very broad m, 1H); 12.25 (broad s, 1H).

Determination of the Activity of the Compounds—Experimental Protocols

1. FAK

The inhibitory activity of the compounds on FAK is determined by measuring the inhibition of autophosphorylation of the enzyme using a time-resolved fluorescence test (HTRF).

The whole cDNA of human FAK, the N-terminal end of which has been labelled with histidine, was cloned in a pFastBac HTc baculovirus expression vector. The protein was expressed and purified to about 70% homogeneity.

The kinase activity is determined by incubating the enzyme (6.6 µg/mL) with different concentrations of test compound in a 50 mM Hepes pH=7.2, 10 mM MgCl$_2$, 100 µm Na$_3$VO$_4$, 15 µM ATP buffer for 1 hour at 37° C. The enzymatic reaction is stopped by adding Hepes pH=7.0 buffer containing 0.4 mM KF, 133 mM EDTA, 0.1% BSA and the labelling is performed, for 1 to 2 hours at room temperature, by adding to this buffer an anti-Histidine antibody labelled with XL665 and a tyrosine phosphospecific monoclonal antibody conjugated to europium cryptate (Eu—K). The characteristics of the two fluorophores are available in G. Mathis et al., Anticancer Research, 1997, 17, pages 3011-3014. The energy transfer from the excited europium cryptate to the acceptor XL665 is proportional to the degree of autophosphorylation of FAK. The long-lasting signal specific for XL-665 is measured in a Packard Discovery plate counter. All the tests are performed in duplicate and the average of the two tests is calculated. The inhibition of the autophosphorylation activity of FAK with compounds of the invention is expressed as a percentage of inhibition relative to a control whose activity is measured in the absence of test compound. To calculate the percentage inhibition, the ratio [signal at 665 nm/signal at 620 nm] is considered.

2. KDR

The inhibitory effect of the compounds is determined in an in vitro test of phosphorylation of substrate with the enzyme KDR via a scintillation technique (96-well plate, NEN).

The cytoplasmic domain of the human KDR enzyme was cloned in the form of a GST fusion protein in the pFastBac baculovirus expression vector. The protein was expressed in the SF21 cells and purified to about 60% homogeneity.

The KDR kinase activity is measured in a 20 mM MOPS, 10 mM MgCl$_2$, 10 mM MnCl$_2$, 1 mM DTT, 2.5 mM EGTA, 10 mM b-glycerophosphate, pH=7.2 buffer, in the presence of 10 mM MgCl$_2$, 100 µm Na$_3$VO$_4$, 1 mM NaF. 10 µl of the compound are added to 70 µL of kinase buffer containing 100 ng of KDR enzyme at 4° C. The reaction is initiated by adding 20 µL of solution containing 2 µg of substrate (SH2-SH3 fragment of PLCγ expressed in the form of a GST fusion protein), 2 µCi of γ$^{33}$P[ATP] and 2 µm of cold ATP. After incubation for one hour at 37° C., the reaction is stopped by adding 1 volume (100 µl) of 200 mM EDTA. The incubation buffer is removed, and the wells are washed three times with 300 µL of PBS. The radioactivity in each well is measured using a Top Count NXT radioactivity counter (Packard).

The background is determined by measuring the radioactivity in four different wells containing radioactive ATP and the substrate alone.

A total activity control is measured in four different wells containing all the reagents (γ$^{33}$P-[ATP], KDR and substrate PLCγ), but in the absence of compound.

The inhibition of the KDR activity with the compound of the invention is expressed as a percentage of inhibition of the control activity determined in the absence of compound.

Compound SU5614 (Calbiochem) (1 µm) is included in each plate as an inhibition control.

3. Tie2

The coding sequence of human Tie2 corresponding to the amino acids of the intracellular domain 776-1124 was generated by PCR using the cDNA isolated from human placenta as a model. This sequence was introduced into a pFastBacGT baculovirus expression vector in the form of a GST fusion protein. The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM MgCl$_2$, 10 mM MnCl$_2$, 1 mM DTT, 10 mM of glycerophosphate. In a 96-well FlashPlate plate maintained on ice, a reaction mixture is deposited, composed of 70 µL of kinase buffer containing 100 ng of enzyme GST-Tie2 per well. Next, 10 µL of the test molecule diluted in DMSO to a maximum concentration of 10% are added. For a given concentration, each measurement is performed four times. The reaction is initiated by adding 20 µL of solution containing 2 µg of GST-PLC, 2 µm of cold ATP and 1 µCi of $^{33}$P[ATP]. After incubation for one hour at 37° C., the reaction is stopped by adding 1 volume (100 µl) of EDTA 200 mM. After removal of the incubation buffer, the wells are washed three times with 300 µL of PBS. The radioactivity is measured on a MicroBeta1450 Wallac.

The inhibition of the Tie2 activity is calculated and expressed as a percentage of inhibition relative to the control activity determined in the absence of compound.

TABLE 1

| Structure | Example | FAK IC 50 (nM) | KDR IC 50 (nM) | TIE2 IC 50 (nM) |
|---|---|---|---|---|
| 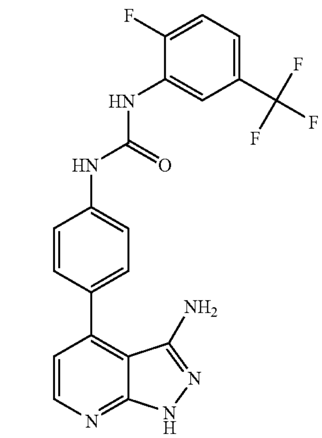 | 1 | 264 | 50 | 8 |
| 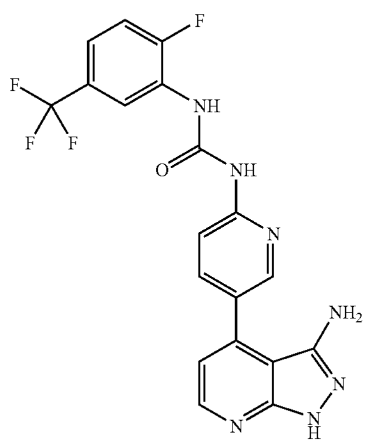 | 2 | 150 | 940 | 23 |
| 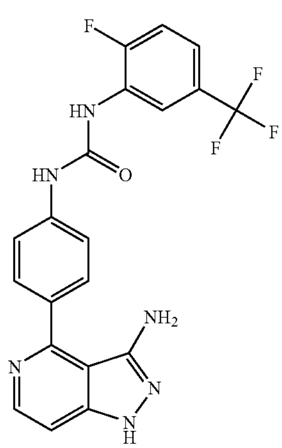 | 3 | 73 | 33 | 5 |

TABLE 1-continued

| Structure | Example | FAK IC 50 (nM) | KDR IC 50 (nM) | TIE2 IC 50 (nM) |
|---|---|---|---|---|
| (structure) | 4 | 80 | 218 | 4 |
| (structure) | 5 | 286 | 49 | 15 |
| (structure) | 6 | 190 | 1855 | 27 |

TABLE 1-continued
| Structure | Example | FAK IC 50 (nM) | KDR IC 50 (nM) | TIE2 IC 50 (nM) |
|---|---|---|---|---|
| 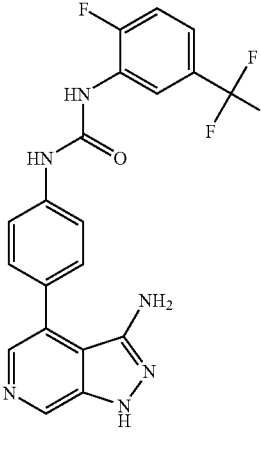 | 7 | — | 36 | 9 |
| 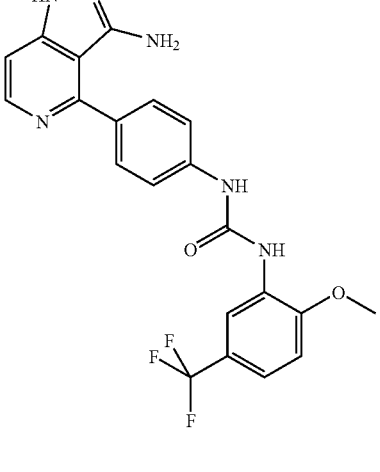 | 10 | — | 60 | 10 |
| 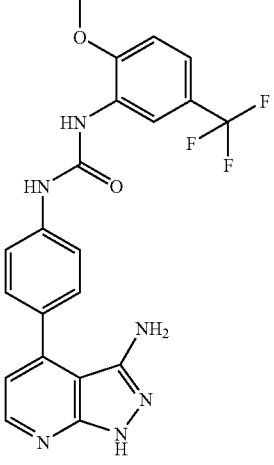 | 14 | — | 24 | 21 |

What is claimed is:

1. A compound of formula (I):

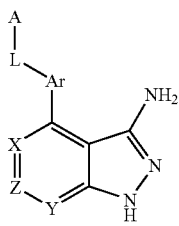

Formula (I)

in which:
1) A is selected from the group consisting of: aryl, heteroaryl, substituted aryl, substituted heteroaryl, cycloalkyl, substituted cycloalkyl, heterocyclyl, and substituted heterocyclyl;
2) L is selected from the group consisting of: bond, CO, NH, CO—NH, NH—CO, NH—SO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, and O—CO—NH;
3) Ar-L-A is

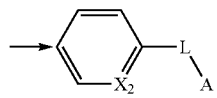

in which X$_2$ is N, which may be substituted or unsubstituted;
4) one from among X, Y and Z is chosen from N and NO, and two others from among Z, Y and X are C(R5) and C(R6);
5) R5 and R6 are independently selected from the group consisting of: H, halogen, R2, CN, O(R2), OC(O)(R2), OC(O)N(R2)(R3), OS(O$_2$)(R2), N(R2)(R3), N═C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(═N(R3))(R2), C(═N(OR3))(R2), S(R2), S(O)(R2), S(O$_2$)(R2), S(O$_2$)O(R2), and S(O$_2$)N(R2)(R3); in which each R2, R3 and R4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl; in which R2 and R3 may be linked together to form a 4- to 8-membered ring containing from 1 to 3 hetero atoms chosen from O, N and S;

or a pharmaceutically acceptable salt thereof.

2. A compound according to claim 1, wherein R5 and R6 are independently selected from H, halogen, OMe and methyl.

3. A compound according to claim 2, wherein R5 and R6 are selected from H and F.

4. A compound according to claim 1, wherein L-A is chosen from NH—CO—NH-A and NH—SO$_2$-A.

5. A compound according to claim 2, wherein L-A is NH—CO—NH-A.

6. A compound according to claim 1, wherein A is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl; optionally substituted.

7. A compound according to claim 4, wherein A is chosen from phenyl, pyrazolyl and isoxazolyl; optionally substituted.

8. A compound according to claim 2, wherein A is substituted with a substituent selected from a first group consisting of (C1-C6)alkyl, (C1-C6)haloalkyl, (C2-C6)alkylene, (C2-C6)alkynyl, aryl, halogen, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen and O—(C1-C3)alkyl.

9. A compound according to claim 5, wherein A is substituted with a substituent selected from a first group consisting of (C1-C6)alkyl, (C1-C6)haloalkyl, (C2-C6)alkylene, (C2-C6)alkynyl, aryl, halogen, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen and O—(C1-C3)alkyl.

10. A compound according to claim 2, wherein A is substituted with a substituent selected from a second group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)alkyl-OH, (C1-C3)alkyl-NH$_2$, (C1-C3)alkyl-COOM, and (C1-C3)alkyl-SO$_3$M; in which, when R8 and R9 are simultaneously other than H, they may be linked to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

11. A compound according to claim 6, wherein A is substituted with a substituent selected from a second group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH and N(R8)(R9); in which R8 and R9 are independently chosen from H, (C1-C3)alkyl, (C1-C3)alkyl-OH, (C1-C3)alkyl-NH$_2$, (C1-C3)alkyl-COOM, and (C1-C3)alkyl-SO$_3$M; in which, when R8 and R9 are simultaneously other than H, they may be linked to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

12. A compound according to claim 2, wherein A is phenyl or isoxazolyl substituted with halogen, (C1-C4)alkyl, (C1-C3)haloalkyl, O—(C1-C4)alkyl, S—(C1-C4)alkyl, O—(C1-C4)haloalkyl or S—(C1-C4)haloalkyl.

13. A compound according to claim 6, wherein A is phenyl or isoxazolyl substituted with halogen, (C1-C4)alkyl, (C1-C3)haloalkyl, O—(C1-C4)alkyl, S—(C1-C4)alkyl, O—(C1-C4)haloalkyl or S—(C1-C4)haloalkyl.

14. A compound according to claim 2, wherein A is substituted with one or more substituents, which may be identical or different, independently selected from the group consisting of F, Cl, Br, I, OH, SH, SO$_3$M, COOM, CN, NO$_2$, CON(R8)

(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9), (C1-C6)alkyl, (C2-C6)alkylene, (C2-C6)alkynyl, aryl, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen, and O—(C1-C3)alkyl; in which R8 and R9 are independently chosen from H, (C1-C3)alkyl, (C1-C3)alkyl-OH, (C1-C3)alkyl-NH$_2$, (C1-C3)alkyl-COOM, and (C1-C3)alkyl-SO$_3$M; in which, when R8 and R9 are simultaneously other than H, they may be linked to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

15. A compound according to claim 6, wherein A is substituted with one or more substituents, which may be identical or different, independently selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9), (C1-C6)alkyl, (C2-C6)alkylene, (C2-C6)alkynyl, aryl, heteroaryl, O—(C1-C6)alkyl, O-Aryl, O-heteroaryl, S—(C1-C6)alkyl, S-Aryl and S-heteroaryl, each being optionally substituted with one or more substituents chosen from (C1-C3)alkyl, halogen, and O—(C1-C3)alkyl; in which R8 and R9 are independently chosen from H, (C1-C3)alkyl, (C1-C3)alkyl-OH, (C1-C3)alkyl-NH$_2$, (C1-C3)alkyl-COOM, and (C1-C3)alkyl-SO$_3$M; in which, when R8 and R9 are simultaneously other than H, they may be linked to form a 5- to 7-membered ring containing from 0 to 3 hetero atoms chosen from O, N and S; in which M is H or a cation of an alkali metal chosen from Li, Na and K; and in which R10 is H or an optionally substituted non-aromatic heterocycle, containing 2 to 7 carbon atoms and 1 to 3 hetero atoms chosen from N, O and S.

16. A compound according to claim 8, wherein A is 2-fluoro-5-trifluoromethylphenyl or 2-methoxy-5-trifluoromethylphenyl.

17. A compound according to claim 1, selected from the group consisting of:
- 1-[5-(3-Amino-1H-pyrazolo[3,4-b]pyrid-4-yl)pyrid-2-yl]-3-(2-fluoro-5-trifluoro-methylphenyl)urea;
- 1-[5-(3-Amino-1H-pyrazolo[3,4-b]pyrid-4-yl)pyrid-2-yl]-3-(2-methoxy-5-trifluoromethylphenyl)urea;
- 1-[5-(3-Amino-1H-pyrazolo[3,4-b]pyrid-4-yl)pyrid-2-yl]-3-(2-methylcarbonylamino-5-trifluoromethylphenyl)urea;

or a pharmaceutically acceptable salt thereof.

18. A compound according to claim 1, selected from the group consisting of:
- 1-[5-(3-Amino-1H-pyrazolo[4,3-c]pyrid-4-yl)pyrid-2-yl]-3-(2-fluoro-5-trifluoro-methylphenyl)urea;
- 1-[5-(3-Amino-1H-pyrazolo[4,3-c]pyrid-4-yl)pyrid-2-yl]-3-(2-methoxy-5-trifluoromethylphenyl)urea;

or a pharmaceutically acceptable salt thereof.

19. A compound according to claim 1, characterized in that it is:
- 6) in achiral form, or
- 7) in racemic form, or
- 8) enriched in one stereoisomer, or
- 9) enriched in one enantiomer;

and in that it is optionally salified.

20. A pharmaceutical composition comprising a compound according to claim 1, in combination with a pharmaceutically acceptable excipient.

21. A pharmaceutical composition comprising a compound according to claim 17, in combination with a pharmaceutically acceptable excipient.

22. A pharmaceutical composition comprising a compound according to claim 18, in combination with a pharmaceutically acceptable excipient.

23. A method for inhibiting a reaction catalysed by a kinase comprising contacting said kinase with an effective amount of a compound according to claim 1.

24. The method according to claim 23, wherein the kinase is chosen from FAK, KDR and Tie2.

* * * * *